(12) United States Patent
Day

(10) Patent No.: US 10,864,163 B2
(45) Date of Patent: Dec. 15, 2020

(54) THERAPEUTIC AGENTS AND DELIVERY WITH MICROSPHERES

(71) Applicant: UCL Business PLC, London (GB)

(72) Inventor: Richard Michael Day, London (GB)

(73) Assignee: UCL Business LTD, London (GB)

(*) Notice: Subject to any disclaimer, the term of this patent is extended or adjusted under 35 U.S.C. 154(b) by 57 days.

(21) Appl. No.: 15/107,802

(22) PCT Filed: Dec. 22, 2014

(86) PCT No.: PCT/GB2014/053821
§ 371 (c)(1),
(2) Date: Jun. 23, 2016

(87) PCT Pub. No.: WO2015/097464
PCT Pub. Date: Jul. 2, 2015

(65) Prior Publication Data
US 2016/0296472 A1 Oct. 13, 2016

(30) Foreign Application Priority Data

Dec. 23, 2013 (GB) .................................. 1322869.7

(51) Int. Cl.
| | | |
|---|---|---|
| *A61K 31/704* | (2006.01) | |
| *A61K 35/12* | (2015.01) | |
| *A61K 35/15* | (2015.01) | |
| *A61K 35/17* | (2015.01) | |
| *A61K 35/28* | (2015.01) | |
| *A61K 35/30* | (2015.01) | |
| *A61K 35/34* | (2015.01) | |
| *A61K 35/39* | (2015.01) | |
| *A61K 35/44* | (2015.01) | |
| *A61L 27/18* | (2006.01) | |
| *A61L 27/54* | (2006.01) | |
| *A61L 31/10* | (2006.01) | |
| *A61L 31/16* | (2006.01) | |
| *B01J 13/06* | (2006.01) | |
| *A61K 9/16* | (2006.01) | |
| *A61L 31/02* | (2006.01) | |

(52) U.S. Cl.
CPC .......... *A61K 9/1647* (2013.01); *A61K 9/1676* (2013.01); *A61K 9/1682* (2013.01); *A61K 31/704* (2013.01); *A61K 35/12* (2013.01); *A61K 35/15* (2013.01); *A61K 35/17* (2013.01); *A61K 35/28* (2013.01); *A61K 35/30* (2013.01); *A61K 35/34* (2013.01); *A61K 35/39* (2013.01); *A61K 35/44* (2013.01); *A61L 27/18* (2013.01); *A61L 27/54* (2013.01); *A61L 31/022* (2013.01); *A61L 31/10* (2013.01); *A61L 31/16* (2013.01); *B01J 13/06* (2013.01); *A61L 2300/64* (2013.01); *A61L 2420/02* (2013.01)

(58) Field of Classification Search
None
See application file for complete search history.

(56) References Cited

U.S. PATENT DOCUMENTS

| 5,232,843 A | * | 8/1993 | Bosley | ................... | C12N 11/08 |
|---|---|---|---|---|---|
| | | | | | 435/134 |
| 8,476,231 B2 | | 7/2013 | Naughton et al. | | |
| 9,480,718 B2 | | 11/2016 | Fraser et al. | | |
| 2006/0140916 A1 | | 6/2006 | Siani-Rose et al. | | |
| 2010/0131075 A1 | * | 5/2010 | Ludlow | ............... | A61L 27/3804 |
| | | | | | 623/23.66 |
| 2010/0323027 A1 | | 12/2010 | Lim et al. | | |

FOREIGN PATENT DOCUMENTS

WO    2008/155558 A2    12/2008

OTHER PUBLICATIONS

Patrick et al., Tissue Engineering, vol. 5, No. 2, pp. 139-151 (1999).*
Ahmadi et al., Acta Biomaterialia, vol. 7, pp. 1542-1549; electronically published Dec. 25, 2010 (of record).*
Mar. 26, 2015—International Search Report of PCT/GB2014/053821.
Chen et al., "Application of Adipose-Derived Stem Cells in Heart Disease," J. of Cardiovasc. Trans. Res. (2014) 7:651-663.
Parmar et al., "A Novel Method for Differentiation of Human Mesenchymal Stem Cells into Smooth Muscle-Like Cells on Clinically Deliverable Thermally Induced Phase Separation Microspheres," Tissue Engineering: Part C, vol. 21, No. 4, 2015, pp. 404-412.
Aug. 23, 2018 U.S. Non-Final Office Action—U.S. Appl. No. 15/661,437.
Apr. 12, 2018 U.S. Non-Final Office Action—U.S. Appl. No. 15/661,437.
Keshaw et al. "Microporous collagen spheres produced via thermally induced phase separation for tissue regeneration" Acta Biomaterialia 6, pp. 1158-1166, 2010.
Hendow et al. "Novel Biomaterial-Based Approaches for Controlling Secretion of Angiogenic Growth Factors," Poster published in the conference proceedings Apr. 2016.
Hendow et al. "Novel Biomaterial-Based Approaches for Controlling Secretion of Angiogenic Growth Factors," Abstract, published in the conference proceedings Mar. 30, 2016.
Jul. 30, 2019—U.S. Non-Final Office Action—U.S. Appl. No. 15/107,802.
Bhang et al. "Efficacious and Clinically Relevant Conditioned Medium of Human Adipose-derived Stem Cells for Therapeutic Angiogenesis" Molecular Therapy, 22:862-872, 2014.

(Continued)

*Primary Examiner* — Soren Harward
*Assistant Examiner* — Paul D. Pyla
(74) *Attorney, Agent, or Firm* — Banner & Witcoff, Ltd.

(57) ABSTRACT

The invention relates to methods for attaching therapeutic agents to structures produced by thermally induced phase separation as well as methods for coating devices and producing multi-layered microspheres.

12 Claims, 17 Drawing Sheets

(56) References Cited

OTHER PUBLICATIONS

Alfaidy et al. "The Multiple Roles of EG-VEGF/PROK1 in Normal and Pathological Placental Angiogenesis" BioMed Research International, vol. 2014, Year: 2014.
Murphy et al. "Mesenchymal stem cells: environmentally responsive therapeutics for regenerative medicine" Experimental & Molecular Medicine, 45, e54, 2013.
Lecouter et al. "Identification of an angiogenic mitogen selective for endocrine gland endothelium" Nature, 512:877-884, 2001.

* cited by examiner (a)

(b)

(a)

(b)

(a)

(b)

a)

b)

c)

(a)

(b)

(c)

(d)

(e)

(a)

b)

(a)

(b)

(c)

(d)

(e)

(f)

(g)

THERAPEUTIC AGENTS AND DELIVERY WITH MICROSPHERES

The invention relates to methods for attaching therapeutic agents to structures produced by thermally induced phase separation as well as methods for coating devices and producing multi-layered microspheres.

BACKGROUND OF THE INVENTION

Thermally induced phase separation (TIPS) microspheres have been previously described in WO 2008/155558. The resulting structure of the microspheres provides improved characteristics such as mechanical strength and the ability to select pore size and whether or not the microspheres are covered with a skin. TIPS microspheres provide a novel degradable scaffold structure to support tissue growth and can deliver bioactive agents to promote tissue generation. The microspheres utilised in the present invention may be produced by the application of TIPS disclosed in WO 2008/155558 or by any other suitable method. The teaching of WO 2008/155558 is hereby incorporated by reference, especially with reference to the methods used to produce the TIPS microspheres. TIPS enables the rapid formation of evenly sized porous microspheres. TIPS microspheres are polymeric, biodegradable and can be loaded with therapeutics for drug delivery applications. The microspheres can be easily delivered to the required location, they can conform to the irregular shape of tissue cavities, they have predictable degradation times, they can deliver a wide range of drugs and they are cost effective to manufacture.

Cell therapy is an emerging technology but improvements are required in terms of cell expansion, targeted delivery of known cell quantities, and retention of cell viability after implantation. TIPS microspheres offer a solution to these problems by providing a highly effective substrate for expansion of cells, minimally invasive delivery and a conformable, degradable scaffold structure that allows diffusion of nutrients to the implanted cells whilst avoiding the need for cell detachment prior to delivery.

The surface of TIPS microspheres provide a highly effective surface topography for the rapid attachment of cells (Ahmadi et al, Enhanced Attachment, Growth and Migration of Smooth Muscle Cells on Microcarriers Produced Using a Thermally Induced Phase Separation. *Acta Biomaterialia* 2011; 7: 1542-1549). From a clinical perspective, rapid attachment of cells to TIPS microspheres is beneficial. For industrial purposes, shorter attachment times provide improved control of the spatial distribution of cells on the surface of the microspheres. This enables greater control of the phenotypic properties of the attached cells, especially confluence, proliferation/expansion, differentiation and detachment behaviour. These properties will (i) reduce process times and improve industrial efficiencies, and (ii) allow more accurate quantification of the dosage of cells being delivered for therapeutic purposes.

SUMMARY OF THE INVENTION

According to a first aspect of the invention there is provided a method for attaching a therapeutic agent to a hydrophobic structure produced by thermally induced phase separation comprising:
  i) at least partly submerging the structure in a culture medium;
  ii) subsequently contacting the structure with a solvent; and
  ii) attaching the therapeutic agent to the structure.

There is also provided a structure produced by thermally induced phase separation (TIPS) having an attached therapeutic agent obtained by the method as described above.

The formation of the structures by TIPS from hydrophobic polymers generally results in hydrophobic and highly porous structures. The combination of these two features results in TIPS structures floating when placed in aqueous solutions such as culture medium. This characteristic hinders the passive attachment of adherent therapeutic agents, in particular cells in suspension, to the surface of the TIPS structures. Therefore, to maximize the efficiency of therapeutic agent attachment, TIPS structures may be at least partly submerged in a culture medium, which will allow the adherent cells to attach to the surface of the microspheres.

TIPS microspheres float for several hours when placed straight into culture medium alone. Wetting of PLGA based structures with ethanol has previously been described (Mikos, A. G. et al. (1994). Wetting of poly(L-lactic acid) and poly(DL-lactic co-glycolic acid) foams for tissue culture. *Biomaterials* 15(1), 55-58). The recognised prior art wetting techniques for PLGA based materials involve immersing the structure in alcohol (typically ethanol) followed by washing to remove the excess alcohol before placing them in an aqueous solution. When this approach is applied to TIPS structures, they become rapidly clumped together due to the polymer being plasticized and they cannot be dispersed. This problem is particularly evident with microspheres which are difficult to disperse into single microspheres. To overcome this problem, it was surprisingly found that TIPS structures can be partly submerged in a culture medium prior to the addition of alcohol. This prevents the structures clumping together and improves their sinking in solution and the subsequent attachment of therapeutic agents to the structures. Furthermore, this approach enables mixing of the therapeutic agent with the TIPS structures immediately prior to administration to site of need, thus eliminating complex manufacture and storage means.

According to a second aspect of the present invention there is provided a hydrophobic structure produced by thermally induced phase separation and treated to improve attachment of a therapeutic agent, comprising:
  i) at least partly submerging the structure in a culture medium; and
  ii) subsequently contacting the structure with a solvent.

A structure obtained by the method according to the second aspect of the present invention has been treated so that it is ready for attachment to a therapeutic agent.

According to a third aspect of the invention there is provided a cell culture plate or well comprising a barrier of non-adherent material ascending from the base of the plate or well.

According to a fourth aspect of the invention there is provided a method for coating a device with a structure obtained by thermally induced phase separation comprising:
  i) coating the device with a mixture comprising a polymer and a solvent;
  ii) quenching the device having the polymer and solvent coating in a quenching fluid; and
  iii) freeze-drying the coating.

There is also provided a device obtained by said method.

According to a fifth aspect of the invention there is provided a method for producing a multi-layered TIPS microsphere comprising:
  i) expressing two or more compositions, each composition comprising a polymer and solvent, simultaneously from a coaxial nozzle, to form a multilayered polymer droplet, the coaxial nozzle comprising at least two subnozzles positioned coaxially;

ii) placing the resultant polymer droplets in a quenching fluid; and iii) freeze-drying the derived multi-layered microsphere.

There is also provided a multi-layered microsphere obtained by said process.

The multi-layered TIPS microspheres may be used to encapsulate therapeutic agents and administer them in a controlled manner. In particular, the architecture of TIPS microspheres can be controlled by adjusting the type and ratio of polymer and solvent used during the manufacturing process. Pores on the surface of the microspheres open into channels that radiate from the large cavity found towards the centre of TIPS microspheres. The structure of traditional TIPS microspheres allows monophasic controlled release of encapsulated API (Foong et al, Anti-tumor Necrosis Factor-Alpha-Loaded Microspheres as a Prospective Novel Treatment for Crohn's Disease Fistulae. *Tissue Engineering* 2010; 16: 855-864). The present inventor has surprisingly found that one or more therapeutic agents can be delivered in a more controlled manner by producing microspheres that consist of multiple layers of polymer.

DETAILED DESCRIPTION OF THE INVENTION

According a first aspect of the invention there is provided a method for attaching a therapeutic agent to a hydrophobic structure produced by thermally induced phase separation comprising:

i) at least partly submerging the structure in a culture medium;

ii) subsequently contacting the structure with a solvent; and ii) attaching the therapeutic agent to the structure.

The resultant structure may be used in various therapeutic methods as described in WO 2008/155558, hereby incorporated by reference. The present method allows for adhering therapeutic agents to the structure for delivery to a site of need within the body.

The term "hydrophobic" has a clear meaning to one skilled in the art, namely having a low affinity for water.

The structure of the present invention may be any suitable structure, including self-supporting structures. Suitable structures include coatings and microspheres. The coating may be subsequently applied to, or already affixed to a device, preferably a medical device. The device can be any device on which it is desirable to attach a therapeutic agent. For example, the device could be part of a diagnostic kit, apparatus for culturing cells, a chip, etc. Preferably the device is a medical device as discussed in detail below. Preferably the structure is a microsphere.

The term "microsphere" refers to one of a preparation of uniform substantially spherical particles. The term is well known in the art. Microspheres may contain a number of radial pores. This means that the pores extend from the central part of the microsphere towards the surface, preferably substantially parallel to the radii of the microsphere. The pores are preferably tubular and interconnected. The radial pores provide the microspheres with a level of mechanical strength.

The term "microsphere" as used herein may encompass a spherical particle which is of a size suitable for the attachment of therapeutic agents. Preferably, the microsphere is about 10 to 2000 μm in diameter as characterised by electron microscopy, such as scanning electron microscopy. However, the microsphere may be smaller than 10 μm such as 2, 3, 4, 5, 6, 7, 8 or 9 μm. The diameter of the microsphere may be selected according to the type of therapeutic agent to be attached. For example, the microsphere may be around 10 to 20 μm in diameter for use in inhalation or drug delivery, or may be around 200 to 600 μm in diameter, especially between 300 and 400 μm in diameter, for tissue engineering. The pore size may also be selected according to the intended use and required mechanical strength and may be selected depending on diameter of the microsphere. Further, the pores are preferably regular in size, that is to say the pores are preferably substantially the same diameter, i.e., the diameter of the pores preferably differs by 10% or less. Porous microspheres have good mechanical strength due to the nature of the pores.

The structure is produced by thermally induced phase separation. In particular, the structure may be produced by any of the methods disclosed in WO 2008/155558, the disclosure of which is incorporated by reference in its entirety. For example, the method of forming the structure may comprise the steps of:

i) dissolving a polymer in a solvent to form a solution;

ii) quenching the solution in a quenching fluid; and iii) freeze-drying the resulting structure.

The structure comprises a polymer. Any hydrophobic polymer may be used, but the polymer is preferably pharmaceutically acceptable and completely soluble in a solvent. The polymer may be degradable or non-degradable. It may be synthetic or non-synthetic. A combination of polymers can be used, for example, a synthetic polymer used in combination with a non-synthetic polymer. Example polymers include poly(lactide-co-glycolide) (PLGA), poly($\alpha$-hydroxyester), polyanhydrides, polyorthoesters, polyphosphazines, polypropylene fumarate, poly(propylene-fumarate-co-ethylene glycol), polyethylene oxide, polyhydroxybutyrate (PHB) and polyhydroxyvalerate (PHV). Co-polymers of two or more polymers may also be used, especially of PHB and PHV. Others include poly($\alpha$-hydroxyester)-co-PEG copolymer, or co-polymers including a pegylated drug. Natural polymers that may be used include fibrin. Preferably the polymer is not chitosan.

The type of polymer (e.g. permanent or degradable, natural or synthetic), porosity, mechanical strength and size may be selected depending on the use or chosen site of delivery of the structure. For example, degradable material may be preferred where tissue from the site of delivery is to replace the temporary scaffold function of the structure. Most preferably, the polymer is poly(lactide-co-glycolide) (PLGA).

Any appropriate solvent may be used in the production of the structure. The solvent is selected to have a higher freeze temperature higher than the temperature of the quench fluid. Example solvents include dimethylcarbonate, chloroform, acetone, dimethylchloride, tetrahydrofuran and supercritical carbon dioxide.

The quenching fluid used to form the structure may be a liquid or a gas. Example quenching fluids include liquid nitrogen, liquid oxygen, liquid $CO_2$, freon, water, ethanol, methanol.

The solution may be introduced into the quenching fluid using any appropriate method. For example, droplets may be produced using a syringe or a vibrating needle. Alternatively, the solution may be sprayed through an atomiser, using, for example, an aerosol propelled or pumped system, or pulled into the quenching fluid using electrostatic force or coaxial air stream.

As described in WO 2008/155558 therapeutic agents may be encapsulated or incorporated into the TIPS structure.

The first aspect of the invention relates to a method for improving the attachment of a therapeutic agent to a TIPS structure produced as described above.

The term "therapeutic agent" includes cells; proteins or peptides such as antibodies or functional fragments (e.g. binding fragments) thereof; nucleic acids, including oligonucleotides; monosaccharides, disaccharides, polysaccharides and derivatives thereof; carbohydrates; prokaryotic microorganisms; eukaryotic microorganisms; or active pharmaceutical ingredients (APIs). Preferably the agent is a cell or an API. The term API as used herein means a substance which can be used in a finished pharmaceutical product and is intended to furnish pharmacological activity or to otherwise have direct effect in the diagnosis, cure, mitigation, treatment or prevention of disease, or to have direct effect in restoring, correcting or modifying physiological functions in human beings.

In addition to attaching the therapeutic agent to the structure, the therapeutic agent may be encapsulated within the structure. The structure may further comprise encapsulated additives, such as, for example, glasses, glass-ceramics, or ceramics containing, for example $NaH_2PO_4$, $CaCO_3$, $P_2O_5$, and $Ag_2SO_4$.

The method for attaching the therapeutic agent to a TIPS structure involves at least partly submerging the structure in a culture medium and subsequently contacting the structure with a solvent.

Partly submerging herein means that the structure is submerged in the culture medium to a point such that the area of the structure to which the therapeutic agent is subsequently attached, contacts the culture medium.

The term "culture medium" encompasses the following solutions: tissue culture medium, serum, whole blood, saline comprising soluble protein and electrolytes, saline comprising serum, saline comprising a plasma substitute, water comprising soluble protein and electrolytes, water comprising serum, water comprising a plasma substitute, and mixtures thereof. Preferably the culture medium is selected from tissue culture medium, serum, or mixtures thereof.

The tissue culture medium may be selected from Dulbecco's Modified Eagle's Medium (DMEM), Ham's F12, RPMI 1640, Iscove's, McCoy's, StemPro®, or mixtures thereof, including other media formulations readily apparent to those skilled in the art, including those found in *Methods For Preparation of Media, Supplements and Substrate For Serum-Free Animal Cell Culture* Alan R. Liss, New York (1984) and *Cell & Tissue Culture: Laboratory Procedures*, John Wiley & Sons Ltd., Chichester, England 1996, both of which are incorporated by reference herein in their entirety. Preferably the tissue culture medium is DMEM.

Serum is typically a complex solution of albumins, globulins, growth promoters and growth inhibitors. The serum for use in the present invention may be obtained from a human, bovine, chicken, goat, porcine, rabbit, horse or sheep source. The serum may also be selected from autologous serum, serum substitutes, or mixtures thereof. Preferably the serum is human serum or Foetal Bovine Serum (FBS) or Foetal Calf Serum (FCS).

The structures maybe partially or fully submerged in the culture medium. Preferably the structures are fully submerged in the culture medium. Preferably the structures are submerged in tissue culture medium comprising from about 5% to about 95% (v/v) serum, more preferably about 5% to about 50% (v/v) serum, more preferably still from about 10% to about 20% (v/v) serum and most preferably about 10% (v/v) serum.

The method of the present invention preferably includes a mixing step. Preferably the structures are mixed with the culture medium before the addition of the solvent. Preferably the structures are mixed with the culture medium at a ratio of about 1:10 (w/v). Mixing may also occur during addition of the solvent. Preferably the combination of the structures and culture medium is mixed with the solvent. The mixing step is performed to ensure that all the surface of the TIPS structure come into contact with the culture medium, and the solvent. Preferably the mixing step is performed by vortexing. Preferably the mixing occurs for about 5 seconds to about 1 minute.

The solvent used to treat the TIPS structures may be selected from acetic acid, acetone, nitromethane, dioxane, tetrahydrofuran, pyridine, methyl ethyl ketone, DMSO, methyl acetate, halogenated hydrocarbons, glycerine, toluene, formamide, lower alcohols and mixtures thereof. The halogenated hydrocarbons include, but are not limited to, dichloromethane, chloroform, tetrachloroethane and trichloroethane. Lower alcohols include, but are not limited to, methanol and ethanol. Preferably the solvent is a lower alcohol, and most preferably the solvent is ethanol.

The solvent used to treat the TIPS structures may be used in any appropriate amount, for example between about 10% and about 100% (v/v). The solvent may be used in an amount between about 10% and about 90%. Preferably the solvent is used in an amount between about 70% and 100% or about 70% and 90%. The solvent is added to the culture medium comprising the structure. The solvent may be at any suitable strength or concentration apparent to one skilled in the art. The solvent may be pre-diluted in de-ionised water to a strength of about 50%, 60%, 70% or 80%.

Following the addition of the solvent to the culture medium comprising the structure and, preferably following the mixing of the resultant mixture, the mixture is preferably incubated. Incubation may occur at any suitable temperature appropriate to the composition of the microsphere. Preferably, incubation occurs at about 20° C. to about 50° C., preferably at about 30° C. to about 40° C., and more preferably at about 35° C. to about 38° C. Most preferably, incubation occurs at about 37° C. The mixture may be incubated for any suitable length of time which allows for subsequent attachment of the therapeutic agent to the structure. Preferably the mixture is incubated for about 0.5 hour to about 5 hours, more preferably from about 0.5 hours to about 4 hours. The structures typically sink in the mixture within about 0.5 to about 2 hours (depending on the porosity of the structure).

After the treatment described above, the structures may be removed from the culture medium and solvent and placed in fresh culture medium appropriate for the therapeutic agent to be attached. At this stage the treated structures can be stored for subsequent attachment of a therapeutic agent.

The therapeutic agent to be attached to the structure may be cells; proteins or peptides such as antibodies or functional fragments (e.g. binding fragments) thereof; nucleic acids, including oligonucleotides; polysaccharides; carbohydrates; prokaryotic microorganisms; eukaryotic microorganisms; or active pharmaceutical ingredients (APIs). Preferably the agent is a cell or an API. Preferably the API is soluble in aqueous solution. One such example is doxorubicin.

The term "attachment" as used herein encompasses any form of attachment but preferably refers to passive attachment.

The structures as treated above and placed in a culture medium may be placed in any container appropriate for the attachment of the therapeutic agent. Suitable examples include microfuge tubes, centrifuge tubes and cell culture plates. Preferably the container is a cell culture plate. The structures may be added to the container at any density appropriate to allow sufficient contact with the therapeutic agent to be attached. Suitable densities can easily be determined by one skilled in the art.

When the agent to be attached to the structure is a cell, culture medium comprising cells may be subsequently added to the container. The attachment of the cells to the surface of the TIPS structure can be controlled by controlling the density of cells seeded in the container. Cells may be seeded at any suitable density for the size of the container in order to allow appropriate contact with the treated structure. Appropriate densities will be known to one skilled in the art.

Any cell displaying anchorage properties can be attached to the treated structure. Particularly suitable anchorage dependent cells include Müller stem cells, endothelial cells, endothelial progenitor cells, pericytes, CD133+ progenitor cells, CD34+ progenitor cells, smooth muscle cells, epithelial cells, mesangioblasts, myoblasts, muscle precursor cells, islet cells, fibroblasts, mesenchymal stromal cells and cells from the immune system such as dendritic cells, B cells and T cells.

Following addition of the therapeutic agent to the structures, the structures are preferably incubated with the therapeutic agent. Preferably, incubation occurs at about 20° C. to about 50° C., preferably at about 30° C. to about 40° C., and more preferably at about 35° C. to about 38° C. Most preferably, incubation occurs at about 37° C., optionally, in a 5% $CO_2$ incubator. The structures may be incubated for any suitable length of time which allows for attachment of the therapeutic agent to the structure. Preferably the structures are incubated for about 0.5 to about 25 hours, more preferably from about 10 to about 20 hours, and most preferably for about 18 hours.

During the incubation period it is preferable to agitate the structures to ensure maximum adherence of the therapeutic agent. Preferably, static incubation is interspersed with agitation. Preferably the structures are agitated at about 10 to about 500 rpm, preferably about 200 to about 400 rpm and most preferably about 300 rpm. Preferably agitation occurs for about 30 seconds to about 2 minutes per hour of incubation, more preferably for about 1 minute per hour of incubation.

According to a second aspect of the present invention there is provided a hydrophobic structure produced by thermally induced phase separation and treated to improve attachment of a therapeutic agent, comprising:
 i) at least partly submerging the structure in a culture medium; and
 ii) subsequently contacting the structure with a solvent.

The present invention also provides a method for producing a TIPS structure that has been treated to enable improved attachment of a therapeutic agent. The method of producing the treated TIPS structure is as defined with respect to the first aspect of the present invention, except that the step of attaching the therapeutic agent is not performed. Instead the method according to the second aspect of the present invention results in the production of treated TIPS structures that can stored or transported. The therapeutic agent can be attached to the treated TIPS structures subsequently.

According to a third aspect of the invention there is provided a cell culture plate or well comprising a barrier of non-adherent material ascending from the base of the plate or well.

Use of a cell culture plate or well comprising a barrier of non-adherent material ascending from the base of the plate or well can reduce the clumping of TIPS structures towards the centre of the culture plate or well during the incubation periods described above (i.e., incubating the TIPS structures with the solvent or incubating the treated TIPS structures with the therapeutic agent. Clumping can be caused by the agitation of the TIPS structures during incubation.

By "non-adherent" it is meant a material that prevents adhesion of the structures to a cell culture plate surface. Examples include hydrophobic coatings, silane, silicone, agarose, or Teflon®. In a preferred embodiment, the non-adherent material is silicone. Preferably the barrier of non-adherent material ascending from the base of the plate or well has a sloped or curved configuration. Preferably the barrier is in the centre of the plate or well. The barrier may be of any size and shape provided that in use, during agitation, the TIPS structures are free to move around a channel formed between the wall of the plate or well and the barrier.

The barrier may be any shape or size provided it prevents the TIPS structures from forming a clump in the middle of the plate or well. Preferably the barrier is a domed shape protuberance having curved sides.

According to a fourth aspect of the invention there is provided a method for coating a device with a structure obtained by thermally induced phase separation comprising:
 i) coating the device with a mixture comprising a polymer and a solvent;
 ii) quenching the device having the polymer and solvent coating in a quenching fluid; and
 iii) freeze-drying the coating.

The exterior and/or interior surface of a device can be coated by a polymer produced by TIPS. The production of a TIPS treated polymer has been previously described in WO 2008/155558 which is incorporated herein by reference. This approach has been shown to provide controllable features that can be tuned according to the application.

The device may be any instrument, apparatus, appliance, material or other article that is intended for use in a biological system, e.g., a biological sample, cell culture, a human or animal body, etc. Such devices may be used to culture cells, for the diagnosis, prevention, monitoring, treatment, or alleviation of disease or an injury, for the investigation, replacement, or modification of the anatomy or of a physiological process or the control of conception. Preferably the device is a dressing material, scaffold device, conduit, tissue culture surface or membrane, an artificial joint, heart valve, stent or a wound filler. Most preferably, the device is a stent or wound filler.

By "coated" it is meant that a layer of polymer produced by TIPS is formed over the exterior and/or interior surface of the medical device.

Surface coating with the TIPS technology may be applied to devices composed of biological or synthetic materials that are substantially non-soluble in the solvent to be used. Suitable materials include decellularised matrices, metal, alloys, plastic, rubber or glass. Suitable solvents include diemethylcarbonate, chloroform, acetone, dimethylchloride, tetrahydrofuran and supercritical carbon dioxide or other solvents suitable for TIPS processing known to those skilled in the art.

The coating method may comprise a variety of methods that involve surface spraying or dipping the device into the polymer and solvent mixture, followed by quenching in a freezing bath and freeze-drying until the solvent has solidified. The length of time taken for the solvent to solidify will depend on the properties of the solvent, the quenching solution and the thickness of the coating. Preferably the quenching solution has a freezing point below that of the solvent and is selected from liquid nitrogen, liquid oxygen, liquid $CO_2$, freon, water, ethanol, methanol and mixtures thereof. Most preferably, the quenching solution is liquid nitrogen. Alternatively, the device may be impregnated with polymer solution or solvent, followed by quenching and freeze-drying.

By adjusting the polymer, solvent or ratio of polymer:solvent, or the temperature of the quenching solution, different surface features are achievable that can be tailored according to the needs. For example, a smooth surface, peppered with pores of 1 to 5 μm with a chevron like pattern due to the solvent crystallisation is produced using neat PLGA for the TIPS process, whereas a rugged, interconnected and disrupted surface may be produced using water mixed into the polymer solution.

Control of the porous structure of the coating is also achievable by manipulating the direction of the freeze front of the solidifying polymer coating. This can be achieved, for example, by placing the polymer coated device onto a cold surface with a temperature below the freezing point of the solvent. Alternatively, a freezing mandrel can be placed into or around a tubular device coated with polymer solution to initiate freezing from the inside out or outside in, respectively.

The device may comprise a therapeutic agent, defined as discussed above, which may be attached to the exterior of the coating as described in association with the first aspect of the invention or encapsulated within the coating by mixing the therapeutic agent with the polymer and solvent.

The coating technique is fast, non-destructive and applicable to a wide range of materials. In particular, and as discussed in the examples below, a TIPS coating has been applied to metallic stent materials (Example 6), to improve attachment of endothelial cells.

According to a fifth aspect of the invention there is provided a method for producing a multi-layered TIPS microsphere comprising:
 i) expressing two or more compositions, each composition comprising a polymer and a solvent, simultaneously from a coaxial nozzle, to form a multilayered polymer droplet, the coaxial nozzle comprising at least two subnozzles positioned coaxially;
 ii) placing the resultant polymer droplet in a quenching fluid; and
 iii) freeze-drying the derived multi-layered microsphere.

The present inventor has surprisingly discovered that the temporal control of multiple therapeutic agents delivered from TIPS microspheres is achievable by producing microspheres that consist of multiple layers of polymer, each with properties tailored to the delivery requirements. The properties of each layer of the multi-layered microsphere are tailored by adjusting the polymer and solvent composition used to form each layer. The polymer and solvent compositions used can differ by the use of different polymers and/or solvents, or by changing the ratio of the polymer to the solvent used to form each layer.

The method used to form the multi-layered microspheres is based on the method used to form microspheres disclosed in WO 2008/155558. The terms used to define the method for forming the multi-layered microspheres are as defined about when discussing the methods used to form the TIPS microspheres.

Multi-layered TIPS microspheres can be achieved using several methods that exist for coaxial delivery of different polymer solutions designed originally for the manufacture of hollow microspheres or encapsulation of different materials. This includes electrohydrodynamic atomization (Pareta & Edirisinghe, *J R Soc Interface*. 2006 Aug. 22; 3(9): 573-582) or systems incorporating a vibrating nozzle for laminar jet break-up.

In the method according to the fifth aspect of the present invention, the two or more compositions comprising a polymer and a solvent are expressed simultaneously resulting in microspheres composed of multiple layers, each of which has a unique structure depending on the formulation of the two or more compositions.

The microspheres may comprise a hollow core, formed by a transient material such as ice, entrapped gas or a highly soluble material, surrounded by one or more outer layers. Preferably there are at least two outer layers. Such TIPS microspheres therefore comprise discrete layers of polymer that can be used to control the release and/or degradation of the microspheres.

Multi-layering may be used to provide microspheres with temporally different mechanical properties and can be used to control the release of different drugs encapsulated into the different layers. This is beneficial where an initial rapid release of a therapeutic agent is to be followed a more steady release of a second therapeutic agent over a longer period. The therapeutic agent may be mixed with the polymer before the polymer is used to form the microsphere. The first layer may be composed of a polymer (e.g. glycolic acid) designed to degrade rapidly away, leaving behind a more stable, slow release polymer (e.g. PLGA (about 80:20 lactic:glycolic acid or about 50:50 lactic:glycolic acid), pure lactic acid, polycaprolactone, polyurethane or a biological polymer such as collagen). An immediate indication for this approach is as a wound filler material, where the outer polymer layer could release an antibiotic to facilitate initial disinfection of the wound, followed by release of an anti-inflammatory biological to attenuate inflammation. The TIPS microspheres would continue to provide their advantageous structural features proven to facilitate tissue infiltration and healing.

The process can be extended to create hollow cores (e.g. a core created with a transient material such as ice, entrapped gas or a highly soluble material) and an immiscible non-degradable shell material that might be used to deliver drugs, shield cells from host immune response, or prevent cell contamination of biochemical processes.

The process can be modified to increase the number of different layers simply by increasing the number of nozzles mounted on the common axis.

The process may also be adapted in order to coat a medical device with multiple layers of a polymer by dipping or spraying the device in immiscible polymer solutions.

The invention will now be described in detail, by way of example only, with reference to the drawings, in which.

Figure 5:
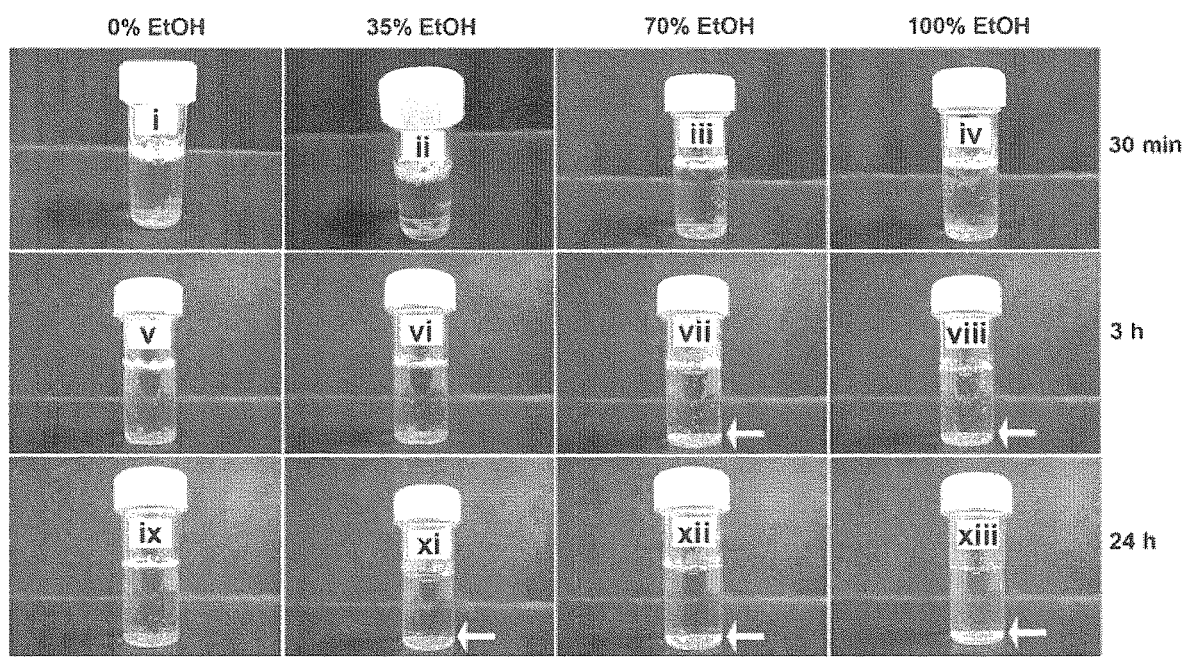

FIG. 5 illustrates that the wetting of TIPS microspheres by ethanol is dose dependent. PLGA microspheres were suspended in medium containing 20% FBS and treated with 0%, 35% (v/v), 70% (v/v) or 100% industrial methylated spirits (containing 99% ethanol [EtOH]), for 30 minutes, 3 hours and 24 hours under incubated culture conditions (37° C., 5% $CO_2$, 95% humidity). Microsphere wetting was dependent on ethanol concentration and the duration of incubation (30 minutes, 3 hours, and 24 hours). Microspheres incubated in 70% (v/v) and 100% ethanol became immersed in medium (containing 20% FBS) after 3 hours, but those exposed to 35% (v/v) ethanol required 24 hours before they were completely submerged. These data demonstrate that PLGA microsphere wetting can be modified to various extents by altering ethanol concentrations and exposure times with this solvent.

Figure 6:
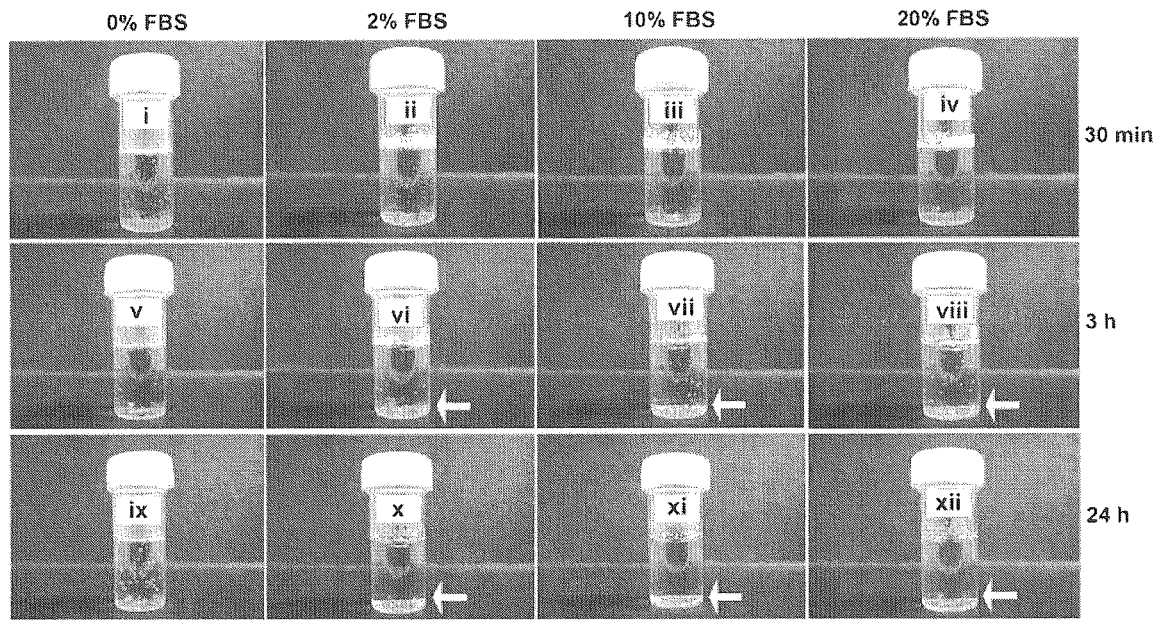
Figure 6:
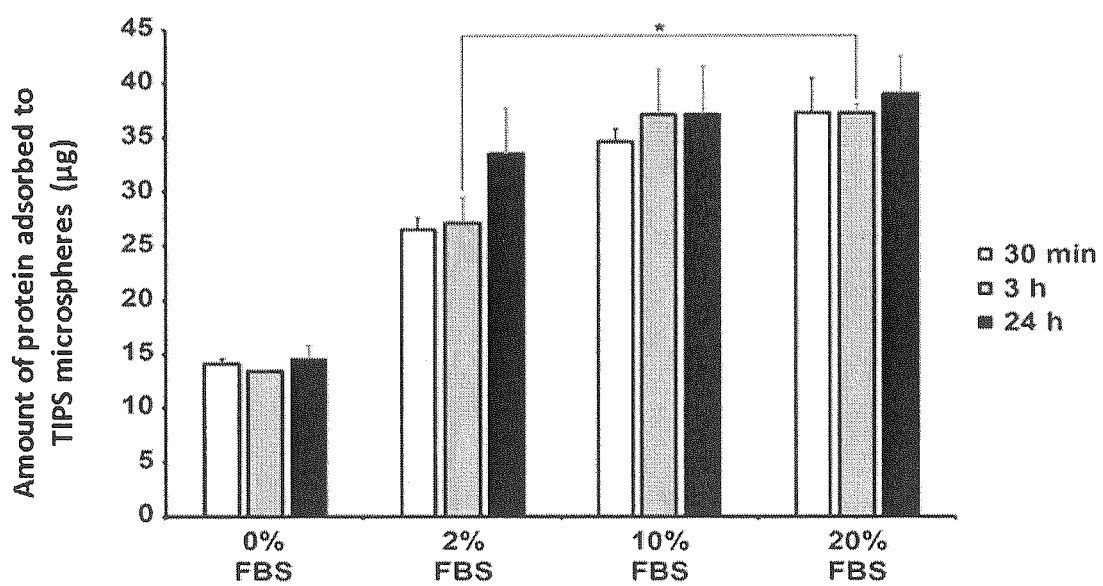

FIG. 6 illustrates that serum proteins adsorb to wetted TIPS microspheres in a dose-dependent manner.

(A) PLGA microspheres were suspended in Dulbecco's Modified Eagle's Medium/F12 (1:1 v/v) containing 0%, 2%, 10% or 20% FBS and treated with 70% (v/v) ethanol (EtOH), for 30 minutes, 3 hours and 24 hours.

(B) The total amount of serum protein adsorbed to microspheres was measured after each incubation period. Data points represent the mean (n=3±S.E.M.) amount of total protein. *$P \leq 0.05$ indicate differences between wetting conditions.

Figure 7:
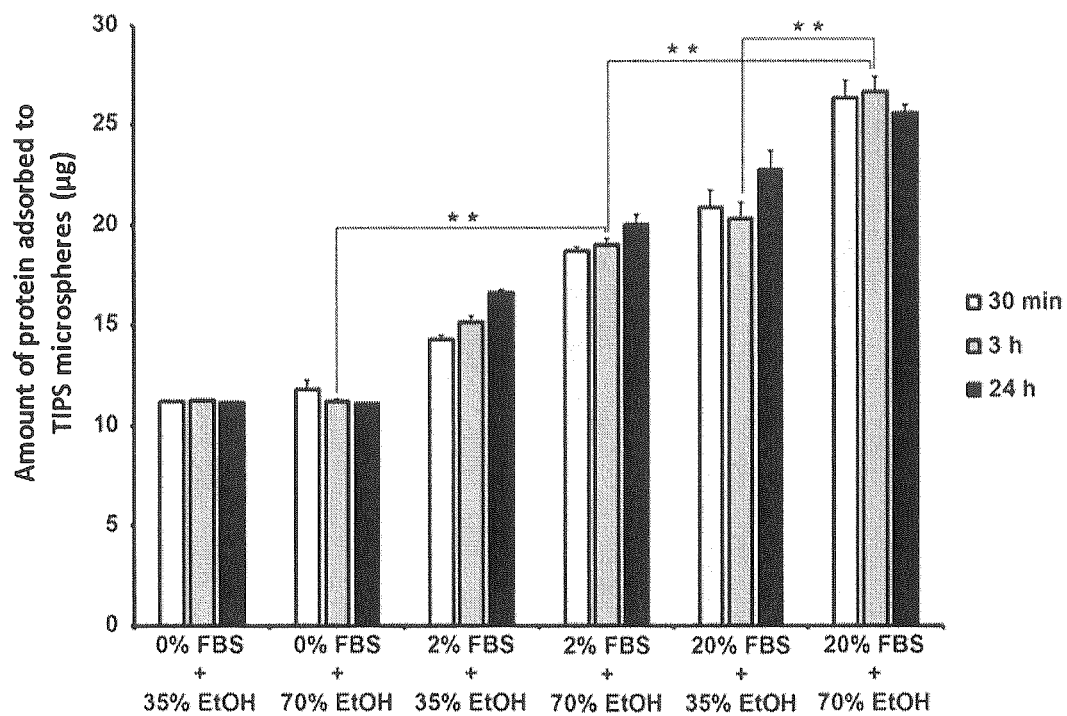
Figure 7:
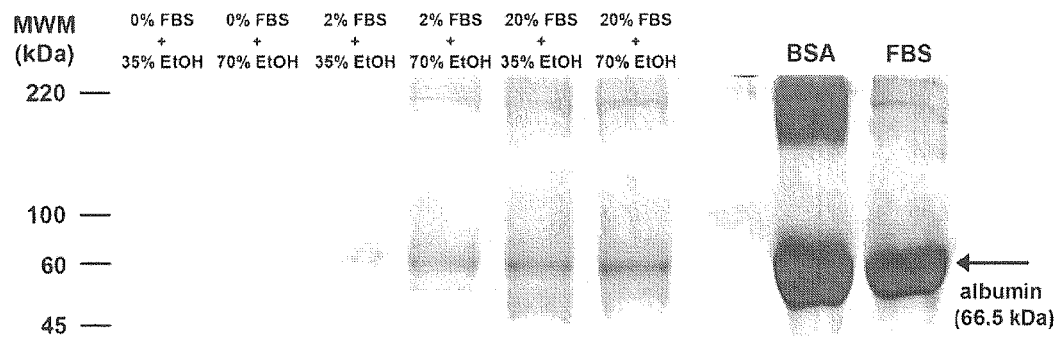

FIG. 7 illustrates that the adsorption of serum proteins to PLGA microspheres is dependent on the extent of pre-wetting.

(A) PLGA microspheres were suspended in Dulbecco's Modified Eagle's Medium/F12 (1:1 v/v) containing 0%, 2% or 20% FBS and treated with 35% (v/v) or 70% (v/v) ethanol (EtOH), for 30 minutes, 3 hours and 24 hours. The total amount of serum protein adsorbed to microspheres was measured after each incubation period. Data points represent the mean (n=3±S.E.M.) amount of total protein. *$P \leq 0.05$ indicate differences between wetting conditions.

(B) Serum and EtOH treated microspheres were heated (95° C.) in Laemmli buffer containing the reducing agent β-mercaptoethanol. Proteins were separated using 15% acrylamide gels and stained using silver nitrate. Bovine serum albumin (BSA) and fetal bovine serum (FBS) were included as external controls.

Figure 8:
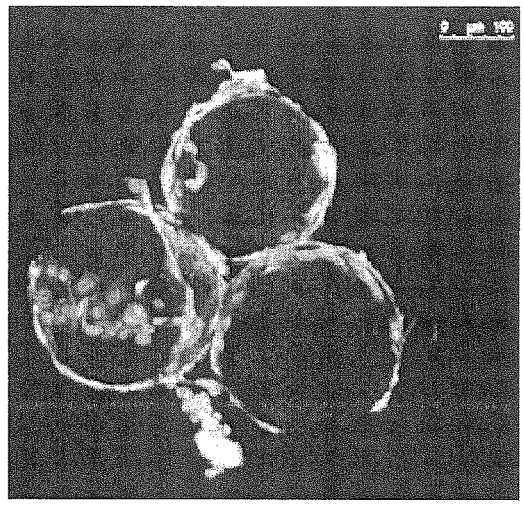
Figure 8:
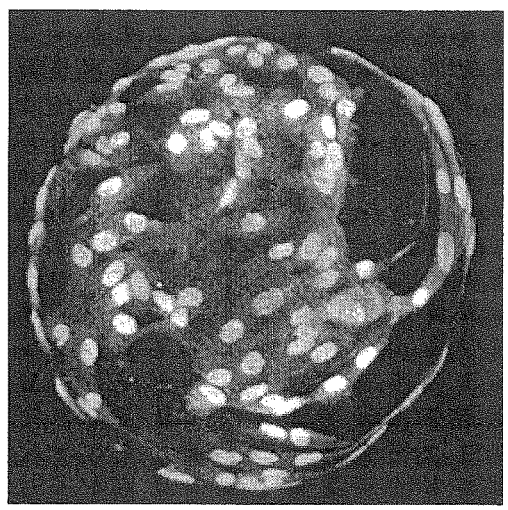
Figure 8:
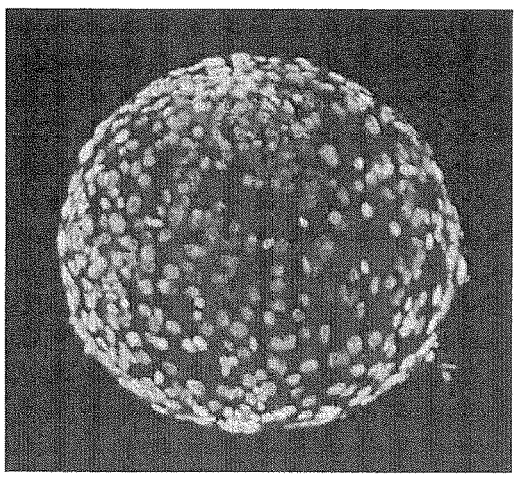

FIG. 8 illustrates cell types shown to attach to the surface of PLGA TIPS microspheres. These include (a) endothelial progenitor cells, (b) smooth muscle cells, and (c) myoblasts.

Figure 9:
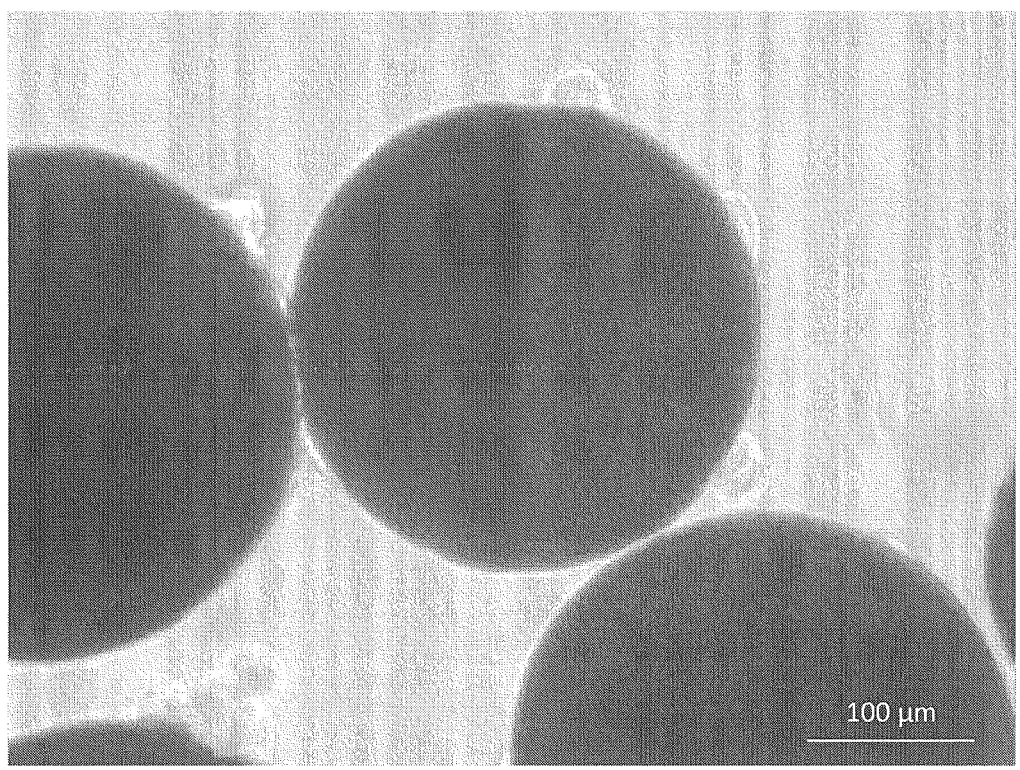

FIG. 9 shows human adipose derived mesenchymal stem cells attached to the surface of TIPS microspheres within 2 hours of incubation.

Figure 10:
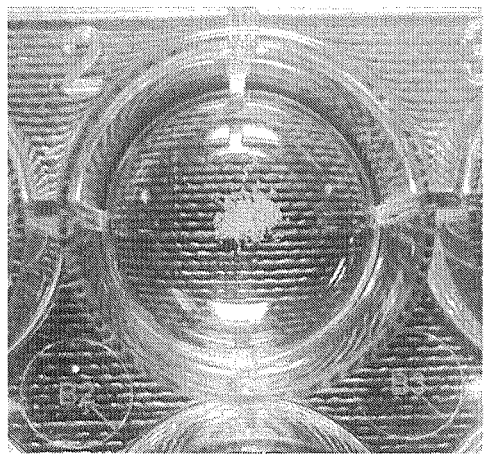
Figure 10:
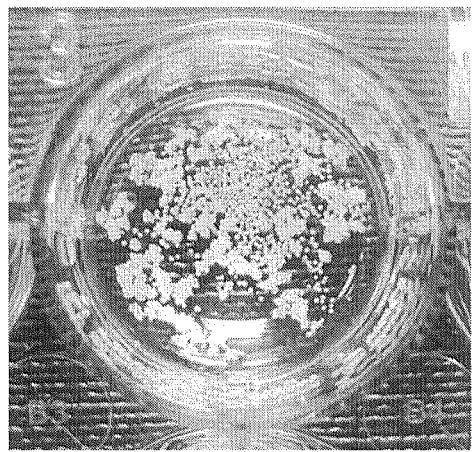
Figure 10:
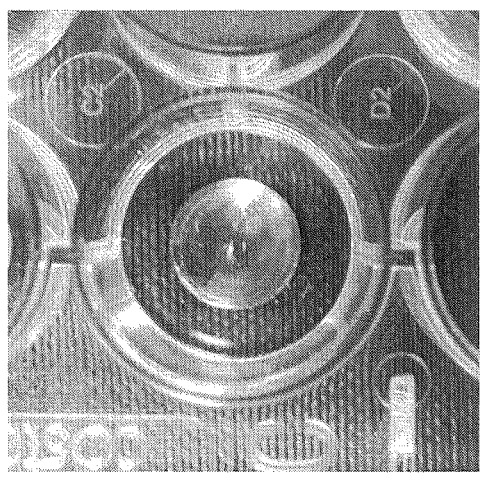
Figure 10:
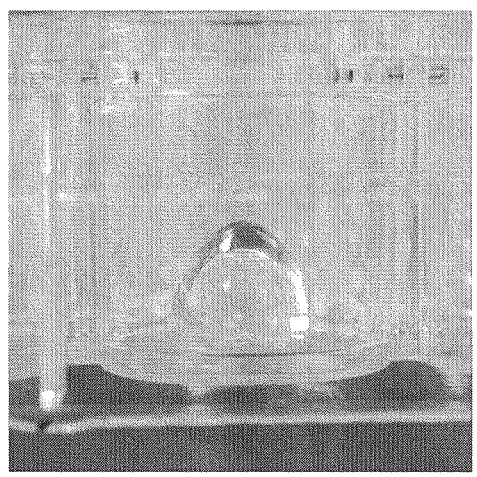
Figure 10:
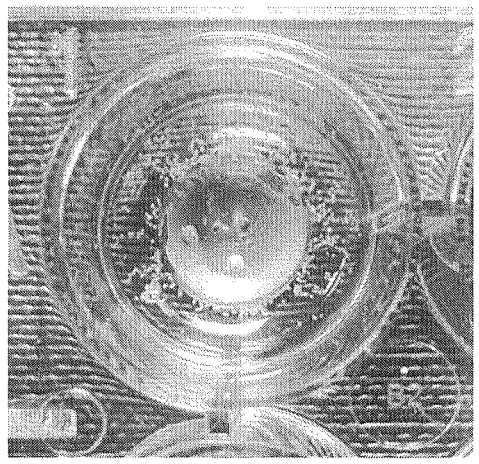

FIG. 10 illustrates TIPS microspheres incubated with cells in LowBind plates attach most efficiently when incubated under static-dynamic conditions (1 hour static incubation followed by 1 min shaking at 300 rpm) (a). This results in the microspheres clustering towards the centre of flat-bottomed wells (b). Clustering of cellularised microspheres in the plates results in cells bridging between adjacent microspheres, forming clumps of microspheres (c-d). Inclusion of a curved low bind surface on the base of the plate prevents the microspheres clustering (e).

Figure 11:
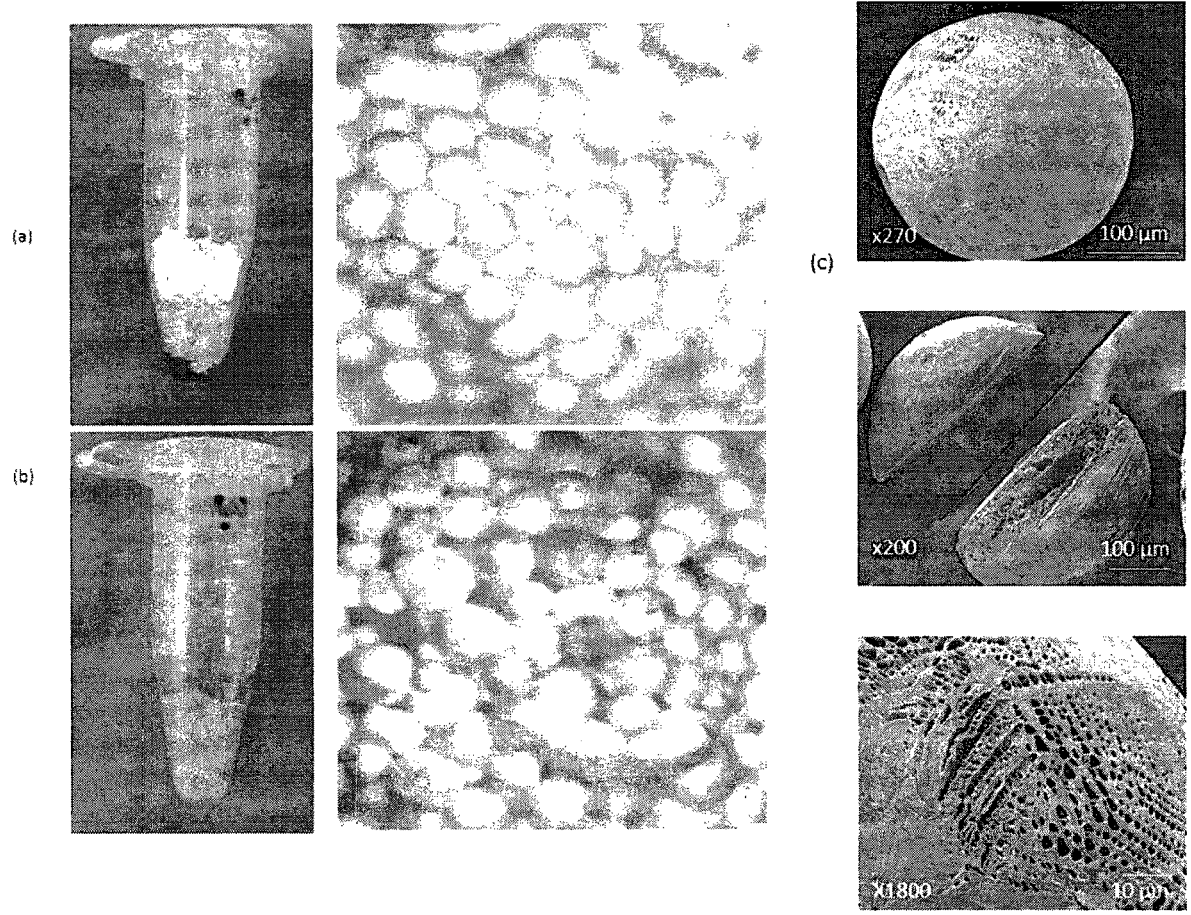
Figure 11:
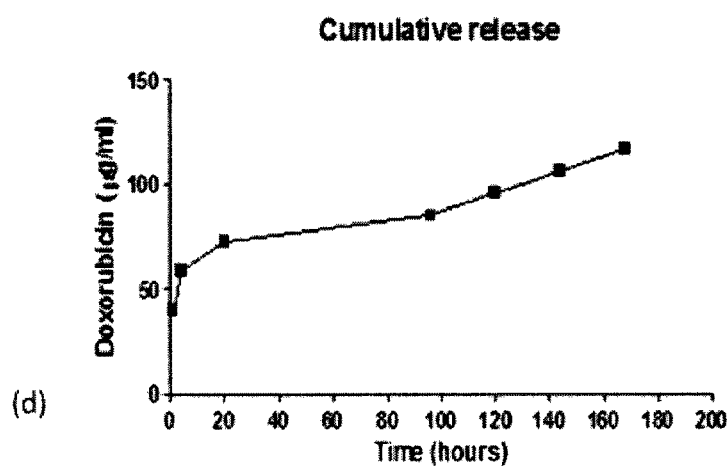

FIG. 11 illustrates that (a) API (doxorubicin) does not bind to the surface of non-wetted, hydrophobic microspheres; (b) doxorubicin binds well to the surface of pre-wetted TIPS microspheres; (c) the unique TIPS microsphere structure of the wetted microspheres remains intact; and (d) controlled release of the API is observed over a prolonged period.

Figure 12:
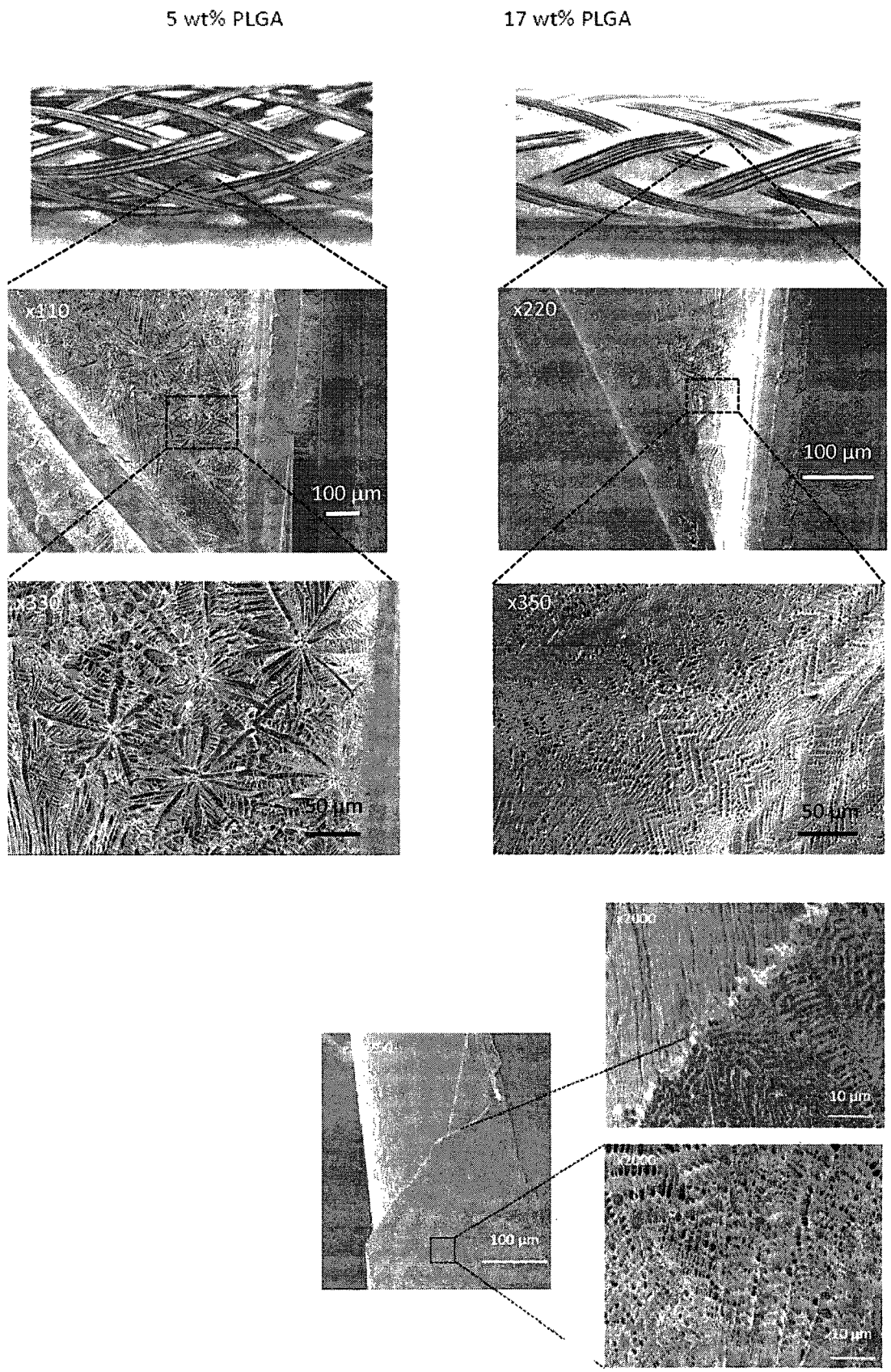

FIG. 12 illustrates metallic surfaces prepared using the TIPS coating method.

Figure 13:
Figure 13:
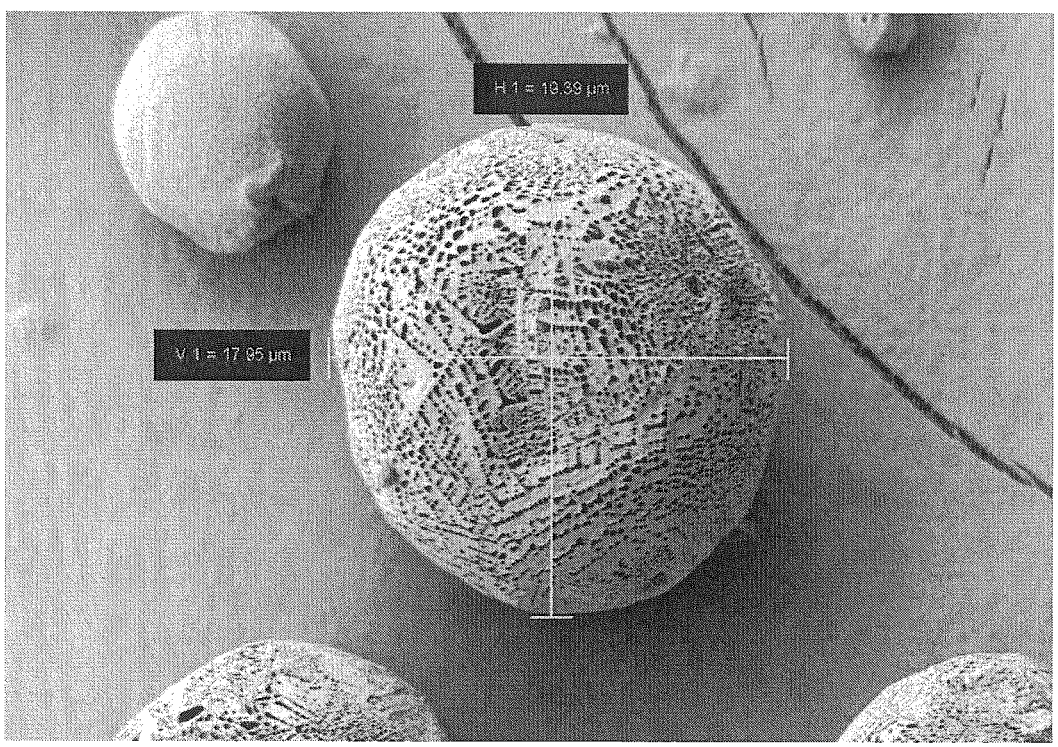

FIG. 13 shows a bare metal cobalt chromium coronary stent coated with TIPS microparticles.

(a) Droplets of poly(lactide-co-glycolide) dissolved in dimethyl carbonate were deposited onto the stent via electrospraying under conditions that resulted in thermally induced phase separation. Shown at 210× magnification.

(b) An individual TIPS microparticle present on the stent surface is shown at a higher magnification (6840×).

Figure 14:
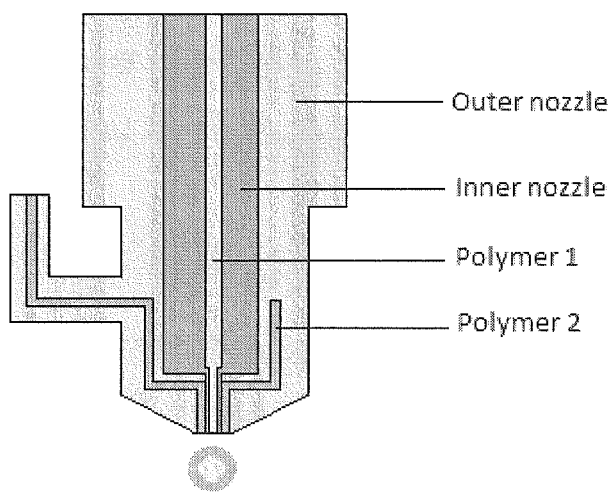

FIG. 14 illustrates a coaxial nozzle delivering two polymer solutions

Figure 15:
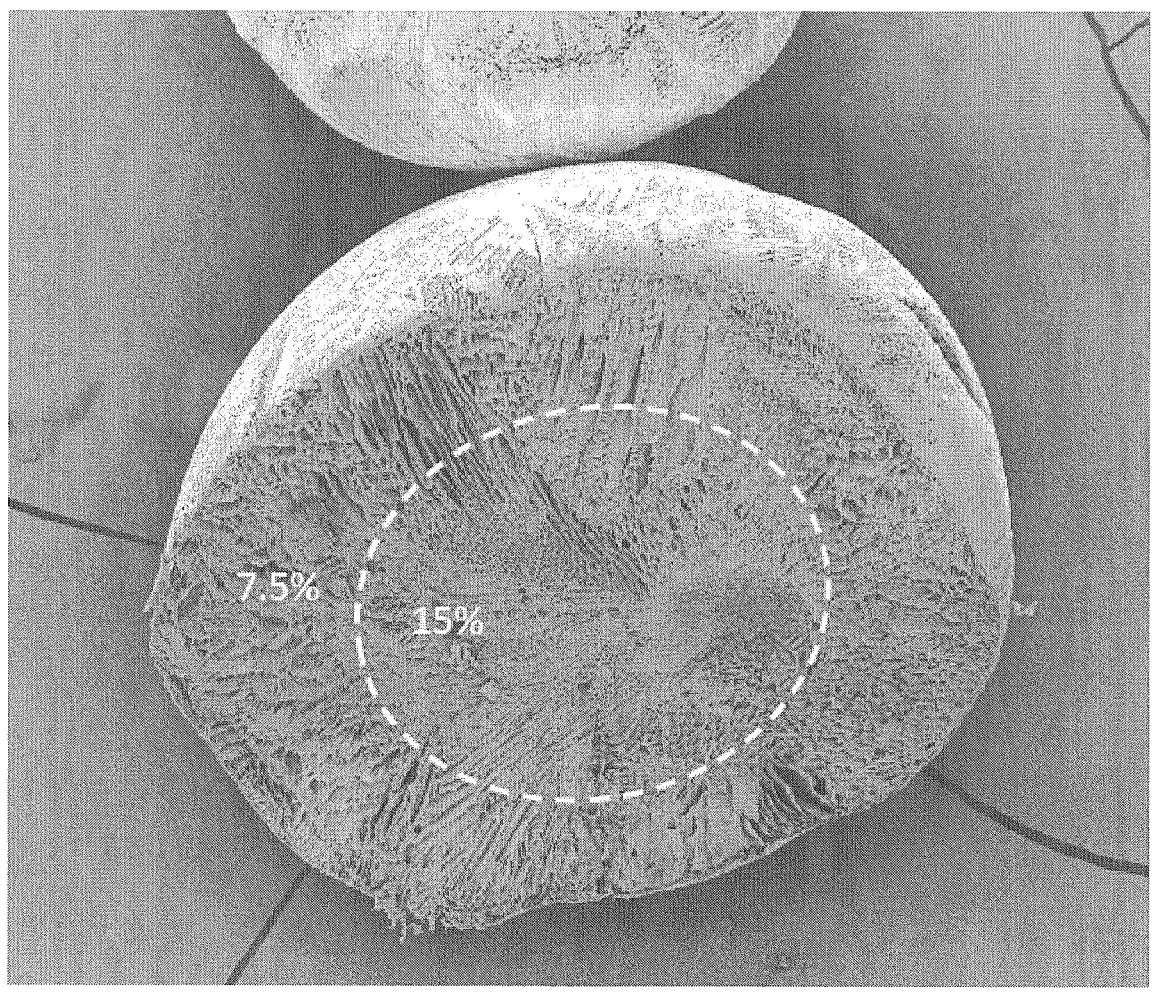

FIG. 15 illustrates a multi-layered microsphere bisected and imaged using scanning electron microscopy. The microsphere comprises an outer shell comprising 7.5% (w/v) PLGA in dimethyl carbonate and an inner core comprising 15% (w/v) PLGA in dimethyl carbonate.

Figure 16:
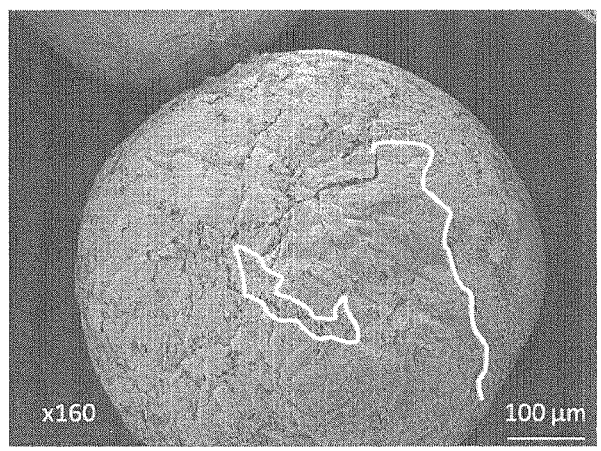
Figure 16:
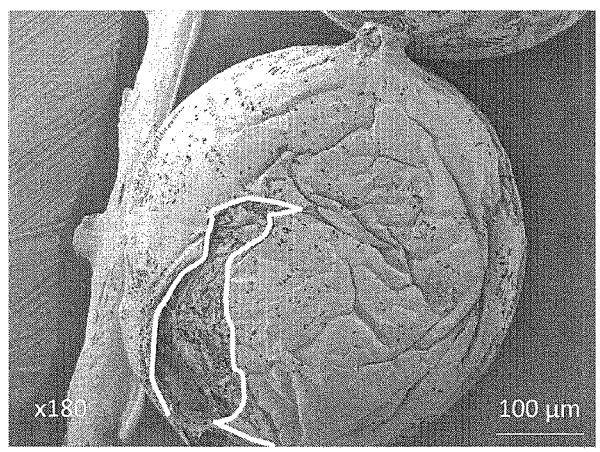
Figure 16:
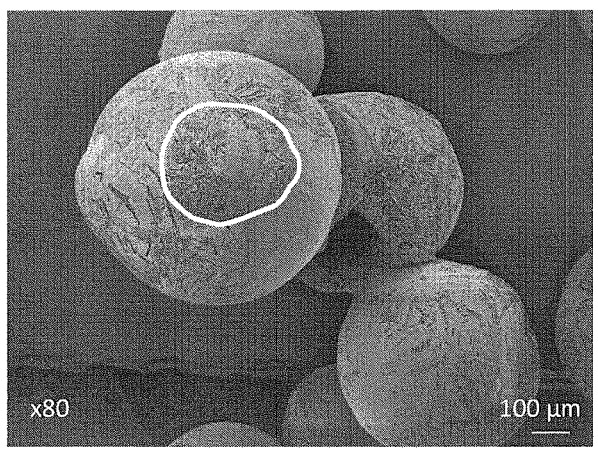
Figure 16:
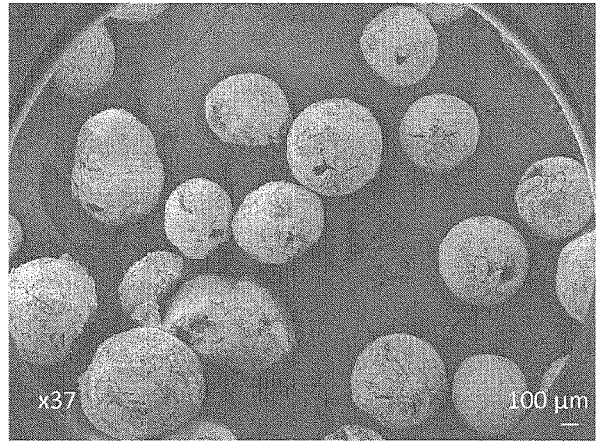
Figure 16:
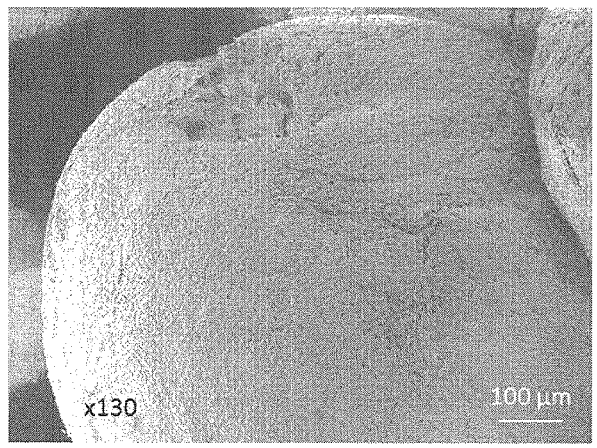
Figure 16:
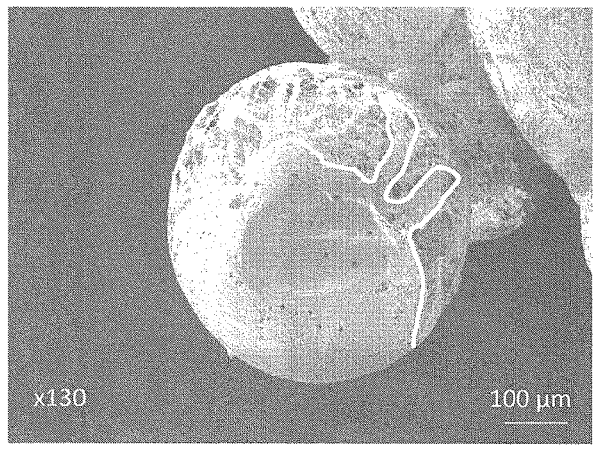
Figure 16:
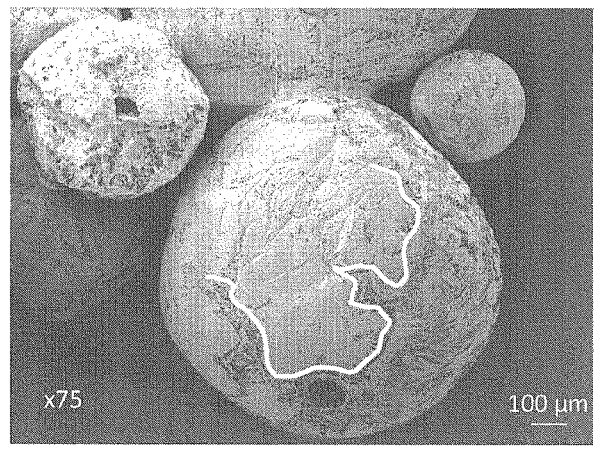

FIG. 16 illustrates SEMs showing TIPS microspheres produced using two different polymers delivered via a coaxial nozzle. Breakage of the distinct outer layer on the surface produced by polymer delivered from the outer nozzle reveals the different physical features of the inner layer produced by polymer delivered from the inner nozzle. The added line indicates the boundaries between the two layers.

(a) Inner nozzle: 4% PEG (polyethylene glycol) dissolved in DMC (dimethyl carbonate) and filtered with 0.45 µm cellulose syringe filters
Outer nozzle: 5% PLGA polymer (75:25) PURASORB PDLG 7502 dissolved in DMC (b-c) Inner nozzle: 4% PLGA polymer (75:25) PURASORB PDLG 7502 dissolved in DMC
Outer nozzle: 5% PEG dissolved in DMC and filtered with 0.45 µm cellulose syringe filters (d) Inner nozzle: 4% PEG dissolved in DMC and filtered with 0.45 µm cellulose syringe filters
Outer nozzle: 5% PLGA polymer (75:25) PURASORB PDLG 7502 dissolved in DMC (e) Inner nozzle: 4% PLGA polymer (75:25) PURASORB PDLG 7502 dissolved in DMC
Outer nozzle: 5% PEG dissolved in DMC and filtered with 0.45 µm cellulose syringe filters (f-g) Inner nozzle: 5% PEG dissolved in DMC and filtered with 0.45 µm cellulose syringe filters
Outer nozzle: 4% PLGA polymer (75:25) PURASORB PDLG 7502 dissolved in DMC

EXAMPLES

Example 1

Production of Microspheres Using the Thermally Induced Phase Separation Process (TIPS Microspheres)

Poly(D,L-lactide-co-glycolide) (PLGA) (75:25) (Medisorb, Alkermes, USA) was used as the polymeric matrix, dissolved in dimethyl carbonate (of >99.9% purity, Sigma Aldrich, UK). PLGA was dissolved in dimethyl carbonate (DMC) at 1:6 w/v (0.833 g PLGA was dissolved in 5 ml DMC for 2 h in a 25 ml Falcon tube, under magnetic stirring). The polymer solution was dripped from a syringe fitted with various sized needle orifices, into liquid nitrogen to rapidly induce the phase separation. Each drop of polymer solution was allowed to equilibrate to the liquid nitrogen temperature, demarked by sinking, prior to the addition of further drops to prevent microsphere agglomeration during processing. The frozen spheres were subsequently freeze-dried overnight to yield the TIPS microspheres. TIPS microspheres were sectioned using a Wilkinson Sword Razor® blade to permit examination of the interior pore structure by scanning electron microscopy (SEM).

Figure 1:
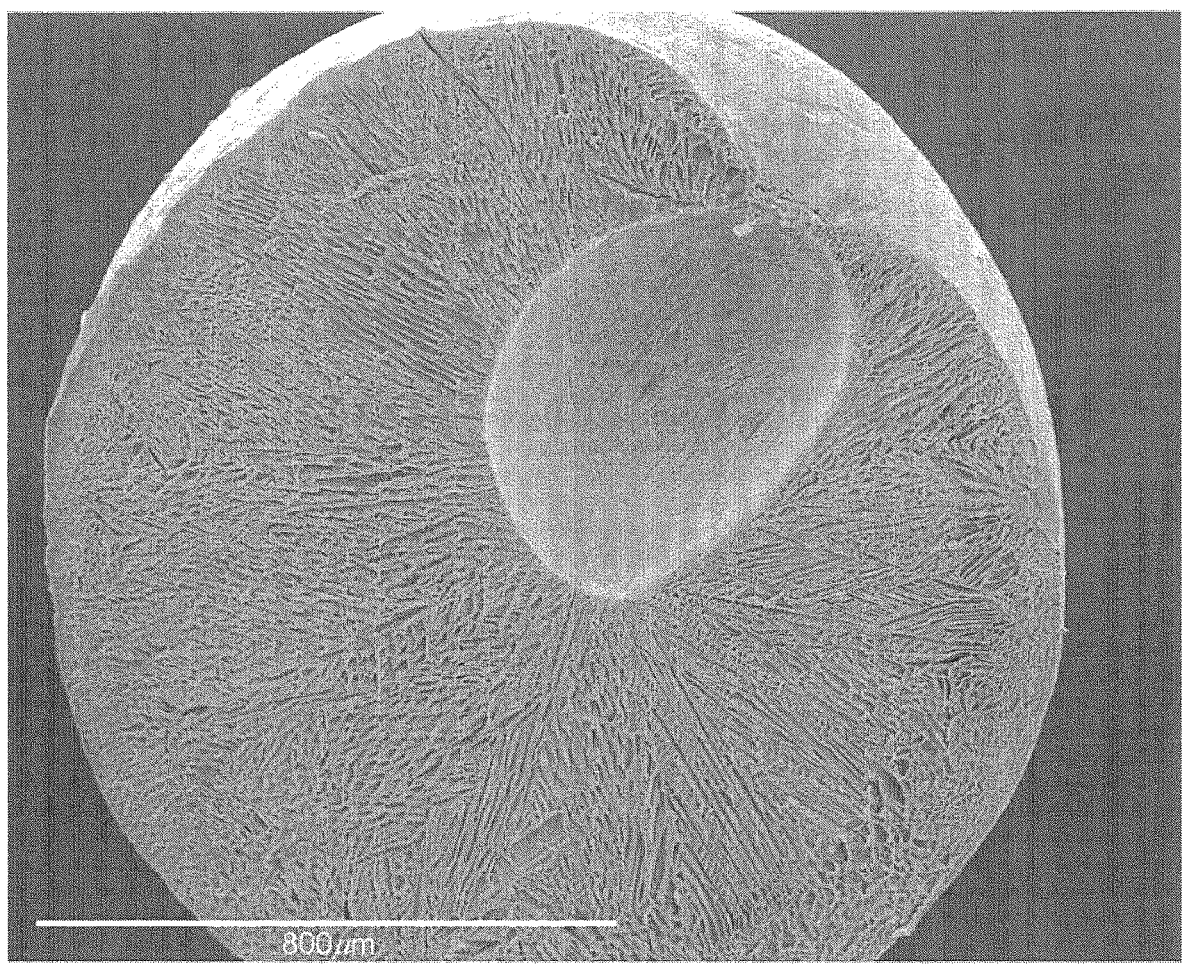
FIG. 1 is a scanning electron microscope (SEM) image of a sectioned microsphere made in accordance with the invention from PLGA. The radial tubular pore structure can be seen.
Figure 2:
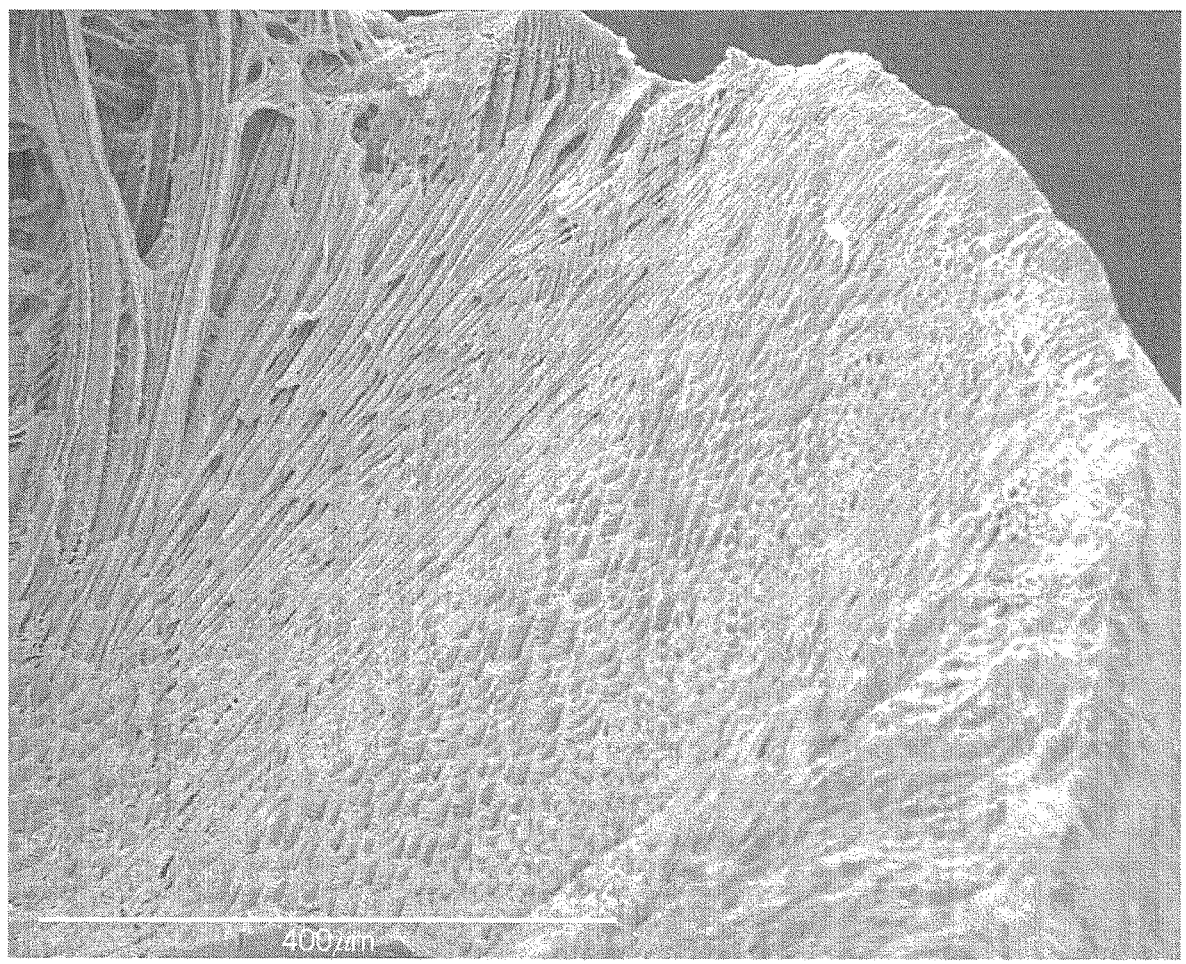
FIG. 2 is a higher magnification SEM image of the microsphere shown in FIG. 1.

The pore structure is highly interconnected with a structure typical of such TIPS foams. Specifically the DMC solvent has a freezing temperature of −1° C. and if the polymer solution is frozen rapidly using liquid nitrogen, tubular pores develop due to the crystallisation front of the freezing solvent. Significantly here, the freeze front is from the outside in; therefore a radial pore structure of tubular pores, interconnected by a ladder-like structure of smaller pores occurred, as shown in FIGS. 1 and 2.

The size of the microspheres is related to the size of the needle orifice, smaller needle orifices give smaller microspheres, as shown in the Table 1, below.

TABLE 1

Effect of needle orifice size on microsphere size

| Needle orifice size | ~Microsphere size |
| --- | --- |
| 700 μm | 1.7 mm |
| 350 μm | 1.2 mm |
| 200 μm | 900 μm |

Figure 3:
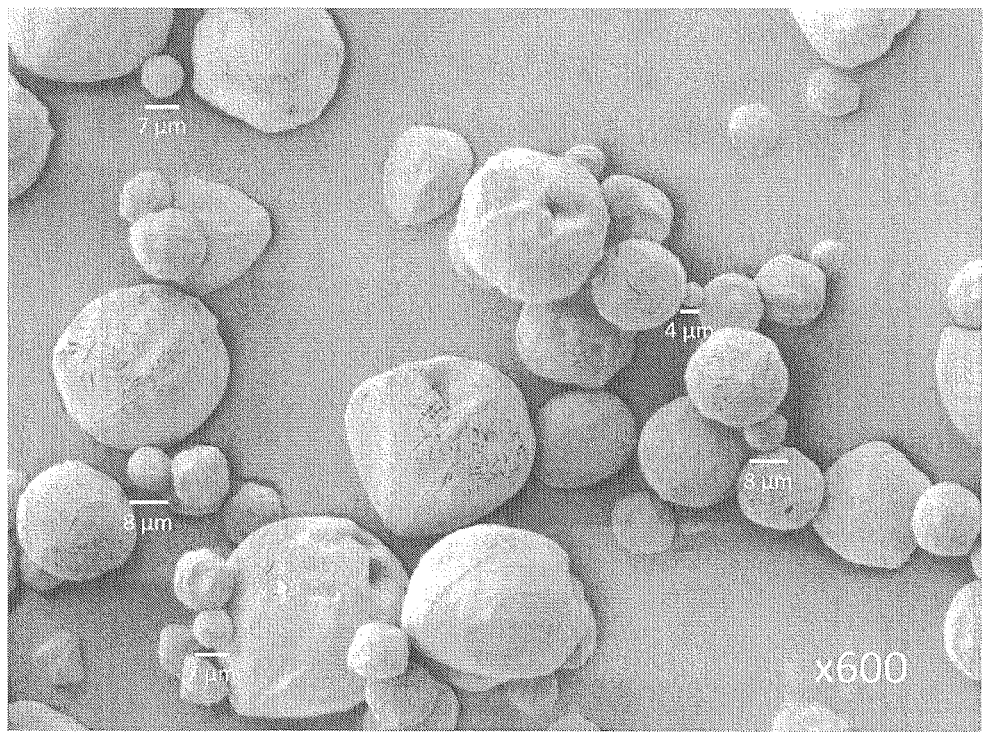
FIG. 3 is SEM images illustrating microspheres smaller than 10 μm at (a) 600× and (b) 400× magnification.
Figure 3:
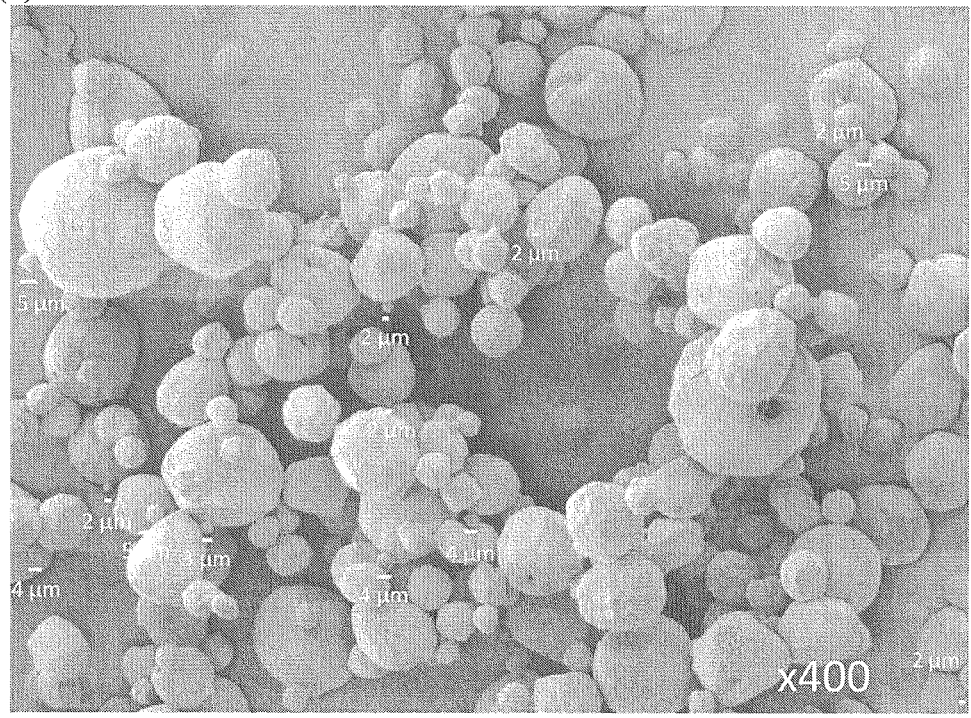

FIG. 3 illustrates microspheres which are smaller than 10 μm, created with a needle orifice size of approximately 690 μm using an electrospraying process.

TIPS microsphere fabrication using dimethyl carbonate as a solvent and rapid quenching in liquid nitrogen resulted in highly ordered interconnected porosity, with radial pores (channel-like) produced from the advancement of the solvent crystallisation front towards the centre of the sphere (parallel to the direction of heat transfer) for a neat PLGA TIPS microsphere. During TIPS the solution is separated into a polymer-rich phase and a polymer-lean phase due to the crystallisation of the solvent, when the temperature of the polymer solution is lower than the freezing point of the solvent and the polymer is expelled from the crystallisation front to form a continuous polymer-rich phase. The solvent is sublimed to leave the pores, which are a three-dimensional fingerprint of the geometry of the solvent crystals. At higher magnification the structure of the neat PLGA TIPS microsphere is observed to have a highly anisotropic channel-like morphology with an internal ladder-like structure, which is a characteristic morphology of foams formed by solid-liquid TIPS. The exterior of the neat PLGA microspheres, composite and protein encapsulated TIPS microspheres consist of a skin region of about 2 μm thickness with a smooth polymer surface, peppered with pores of 1 to 5 μm and covered with chevron like patterns due to the initial freeze front of the solvent across the droplet surface. Once the freeze fronts progress towards the centre of the droplet, the pore structure becomes more ordered, interconnected and ladder-like. The size of the spheres can be controlled by the size of the needle orifice, with smaller spheres produced from needles of narrower orifice (Table 1). The microspheres are monodisperse due to the consistent droplet formation. Voids are evident in the samples and are due to the entrapment of air during the manual droplet formation method, and the short drop distance to the liquid nitrogen used in the current study. The voids consist of a neck extending from the exterior surface of the sphere. Formation of these air pockets might be prevented by the use of a vibrating needle and a more optimized processing technique. The microstructure of the pores and walls can be controlled by varying the polymer concentration, filler loading content, quenching temperature and solvent used. Porosity increases with decreasing polymer concentration and filler content. Foams of up to 95% porosity can be achieved using the TIPS technique. Our method using DMC as solvent and PLGA polymer enables the formation of a slightly dense skin region and radial pores, thereby enhancing the mechanical properties over a random pore structure.

The use of an electromagnetic vibrating needle may be employed to i) maintain dispersion of the particulates in the polymer solution, ii) prevent blocking of the needle and iii) achieve smaller microspheres (100 to 800 μm) by vibrating the nozzle itself. The deviations in sphere size will depend on the density and surface tension of the matrix. Roughly, the smallest achievable drop diameter is 1.5 to 2 times larger than the nozzle diameter used.

Example 2

Wetting of TIPS Microspheres

TIPS microspheres were 'wetted' using the following protocol:
1. Approximately 30 mg of dry TIPS microspheres were placed into a 1.5 ml microfuge tube.
2. 500 μl of foetal calf serum (or tissue culture medium (e.g. Minimum Essential Medium Eagle [Sigma Aldrich M2279]+10% foetal calf serum) was added to microfuge tube.
3. The microfuge was vortexed for 20 seconds to mix the microspheres with the solution.
4. 300 μl of ethanol (diluted to 50, 60, 70 and 80% v/v with de-ionized water) was added to each tube.
5. The microfuge was vortexed for 20 seconds to mix the microspheres with the solution.
6. The microfuge tubes were placed in an incubator at 37° C. for 90 minutes and 240 minutes.
7. The incubation solution was removed from the microfuge tubes and replaced with fresh culture medium appropriate for the cells to be attached.

Figure 4:
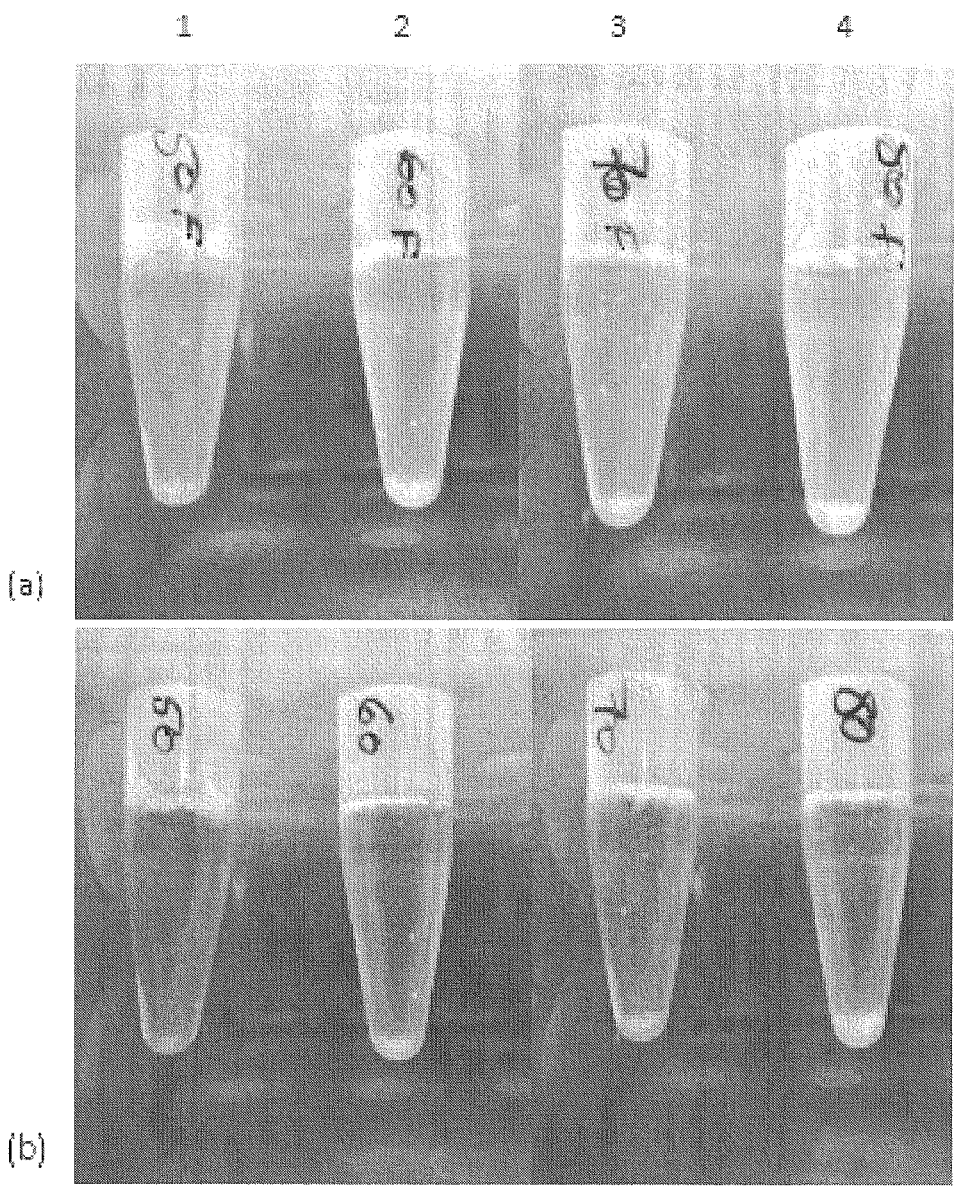
FIG. 4 illustrates microspheres incubated in (a) 500 µl neat serum and (b) microspheres in 500 µl culture medium containing 10% serum prior to addition of 300 µl ethanol (1=50%, 2=60%, 3=70%, 4=80% v/v ethanol in deionised water).

FIG. 4 illustrates microspheres incubated in (a) 500 μl neat serum and (b) microspheres in 500 μl culture medium containing 10% serum prior to addition of 300 μl ethanol (1=50%, 2=60%, 3=70%, 4=80% v/v ethanol in deionised water). The majority of microspheres sunk within 90 minutes incubation at 37° C. The effect is more pronounced at concentrations of ethanol above 60% v/v. All of the microspheres sunk within 4 hours of incubation.

FIG. 5 illustrates that the wetting of TIPS microspheres by ethanol is dose dependent. PLGA microspheres were suspended in medium containing 20% FBS and treated with 0%, 35% (v/v), 70% (v/v) or 100% industrial methylated spirits (containing 99% ethanol [EtOH]), for 30 minutes, 3 hours and 24 hours under incubated culture conditions (37° C., 5% $CO_2$, 95% humidity). Microsphere wetting was dependent on ethanol concentration and the duration of incubation (30 minutes, 3 hours, and 24 hours). Microspheres incubated in 70% (v/v) and 100% ethanol became immersed in medium (containing 20% FBS) after 3 hours, but those exposed to 35% (v/v) ethanol required 24 hours before they were completely submerged. These data demonstrate that PLGA microsphere wetting can be modified to various extents by altering ethanol concentrations and exposure times with this solvent.

FIG. 6 illustrates that serum proteins adsorb to wetted TIPS microspheres in a dose-dependent manner.

(A) PLGA microspheres were suspended in Dulbecco's Modified Eagle's Medium/F12 (1:1 v/v) containing 0%, 2%, 10% or 20% FBS and treated with 70% (v/v) ethanol (EtOH), for 30 minutes, 3 hours and 24 hours.

(B) The total amount of serum protein adsorbed to microspheres was measured using the micro Lowry protein assay after each incubation period. Data points represent the mean (n=3±S.E.M.) amount of total protein.

*$P \leq 0.05$ indicate differences between wetting conditions.

FIG. 7 illustrates that the adsorption of serum proteins to PLGA microspheres is dependent on the extent of pre-wetting.

(A) PLGA microspheres were suspended in Dulbecco's Modified Eagle's Medium/F12 (1:1 v/v) containing 0%, 2% or 20% FBS and treated with 35% (v/v) or 70% (v/v) ethanol (EtOH), for 30 minutes, 3 hours and 24 hours. The total amount of serum protein adsorbed to microspheres was measured using the micro Lowry protein assay after each incubation period. Data points represent the mean (n=3±S.E.M.) amount of total protein. *$P \leq 0.05$ indicate differences between wetting conditions.

(B) Serum and EtOH treated microspheres were heated (95° C.) in Laemmli buffer containing the reducing agent β-mercaptoethanol. Proteins were separated using 15% acrylamide gels and stained using silver nitrate. Bovine serum albumin (BSA) and fetal bovine serum (FBS) were included as external controls.

Example 3

Cell Attachment to TIPS Microspheres

Cells were attached to TIPS microspheres which were wetted using the method described in Example 1 using the following protocol:

1. Wetted TIPS microspheres in fresh culture medium were transferred to wells of a Corning® Costar® Ultra-Low attachment multiwell plate.
2. The culture medium was removed leaving the only wetted microspheres in the wells of the plate.
3. 400 µl of fresh tissue culture medium was added to the wells.
4. 100 µl of medium containing $1 \times 10^5$ cells was added to the wells.
5. The plate was placed on an orbital shaker (STUART SSM5) placed inside a $CO_2$ incubator at 37° C. The shaker was set to agitate the plate at 300 rpm for 1 minute per hour.
6. The plate was incubated for 18 hours before the cellularised microspheres are removed.
7. Cells were stained and imaged by fluorescence microscopy as shown in FIG. 4.

FIG. 8 illustrates cell types shown to attach to the surface of PLGA TIPS microspheres. These include (a) Muller stem cells, (b) endothelial progenitor cells, (c) smooth muscle cells, (d) lung epithelial cells, (e) mesangioblasts, (f) myoblasts.

Cell attachment and delivery both dependent on porosity. Each cell type is suited to different surface textures for attachment, spreading and differentiation. Table 2 illustrates the preferred size ranges and porosity for various clinical conditions.

TABLE 2

Preferred microsphere size ranges and porosity for various clinical conditions

| Clinical Condition | Size Range (µm) | Porosity | Cell Type | Delivery Route |
|---|---|---|---|---|
| Fistula | 100-400 | Medium | Mesenchymal stem cells (MSC; autologous or allogenic) | Into fistula tract via syringe and cannula |
| Vision degeneration | <100 | Medium | Müller stem cells | Injection, spray |
| Large orthopaedic defects | 10-300 | Low Medium | Osteoblasts, chondrocytes and mesenchymal stem cells | Packing, spraying, syringe and cannula |
| Tumour immobilisation and immunotherapy | <10 | Medium High | Dendritic cells, T, lymphocytes | Intravascular |
| Osteoarthritis | 10-300 | Low Medium | MSC | Injection, spray (intra-articular) and intravenously |
| Incontinence | 100-400 | Medium | Myoblasts, MSC | Injection |
| Heart failure | <100 | Medium High | Bone marrow, cardiopoietic cells, cardiac progenitor cells | Intravenously, catheter, intramyocardial |
| Muscular dystrophy | <100 | Low Medium | MSC, mesangioblast, myoblast | Injection, intravenously, packing |
| 3D models and cell expansion | 10-400 | Low Medium High | Adherent cells | Expansion or in vitro modelling in suspension cultures |
| Fermentation/vaccine production/brewing/filtration | 10-500 | Low Medium High | Adherent cells, microorganisms | Alternative to wave bag/cell bag bioreactors, biofiltration medium. |

The use of a low attachment plate during the cell attachment protocol outlined above prevents non-adhered cells attaching to the plate instead of the microspheres. The period of agitation re-suspends cells to increase the likelihood of cells attaching to the sunk microspheres. Experiments show cells attach to TIPS microspheres within 2 hours incubation using the wetting and agitation process. FIG. 9 shows human adipose derived mesenchymal stem cells attached to the surface of TIPS microspheres within 2 hours of incubation.

Example 4

Inclusion of a Curved Low Bind Surface on the Base of the Tissue Culture Plate

Use of a tissue culture plate comprising a barrier of non-adherent material ascending from the base of the wells can reduce clumping of cellularised TIPS microspheres towards the centre of wells in the culture plate. Clumping can be caused by vortexing of the culture medium in the dynamic phase of incubation.

In one embodiment, the tissue culture plate comprises an upward curve of non-adherent silicone material attached to the centre of the well of the low bind tissue culture plate described in Example 3. This prevents the microspheres from clustering and adhering together as illustrated in FIG. 10.

FIG. 10 illustrates TIPS microspheres incubated with cells in LowBind plates attach most efficiently when incubated under static-dynamic conditions (1 hour static incubation followed by 1 min shaking at 300 rpm) (a). This results in the microspheres clustering towards the centre of flat-bottomed wells (b). Clustering of cellularised microspheres in the plates results in cells bridging between adjacent microspheres, forming clumps of microspheres (c-d). Inclusion of a curved low bind surface on the base of the plate prevents the microspheres clustering (e).

Example 5

Attachment of Active Pharmaceutical Ingredients (API) to TIPS Microspheres

The wetting technique described in Example 2 can facilitate the attachment of (API), which are soluble in aqueous solution to TIPS microspheres.

100 mg of TIPS microspheres was added to a 7 ml plastic container. The microspheres were wetted with 70% ethanol for 1 minute. The alcohol was removed and the microspheres washed with 5 ml deionised water. 1 ml of doxorubicin (0.5 mg/ml in water) was added to the container. The microspheres and doxorubicin solution were mixed by pipetting and incubated overnight at room temperature with agitation at 150 rpm on an orbital shaker. Control non-wetted microspheres were treated in the same manner. The microspheres were centrifuged at 13000 rpm for 20 seconds. The doxorubicin remained bound to the surface of the wetted microspheres whereas it was separated from the non-wetted samples.

FIG. 11 illustrates that (a) API (doxorubicin) does not bind to the surface of non-wetted, hydrophobic microspheres; (b) doxorubicin binds well to the surface of pre-wetted TIPS microspheres; (c) the unique TIPS microsphere structure of the wetted microspheres remains intact; and (d) controlled release of the API is observed over a prolonged period.

Example 6

Coating of a Metallic Scaffold

The following example describes the method for coating a metallic scaffold (hereafter termed 'scaffold'):
 1. The scaffold material was immersed into a solution of 5 wt % poly(lactide-co-glycolide) dissolved in dimethyl carbonate for 1 minute.
 2. The coated scaffold material was immediately placed into a container of liquid nitrogen resulting in separation of the polymer solution into polymer rich and polymer lean phases.
 3. The frozen coated scaffold was placed into a freeze drier and lyophilized for 24 hours until removal of the solvent was complete.
 4. The coated scaffold was imaged using scanning electron microscopy (FIG. 12).

FIG. 13 shows a bare metal cobalt chromium coronary stent coated with TIPS microparticles. Droplets of poly(lactide-co-glycolide) dissolved in dimethyl carbonate were deposited onto the stent via electrospraying under conditions that resulted in thermally induced phase separation. After droplets were deposited by electrospraying, the method of FIG. 12 from step 2 onwards was followed.

Example 7

Creation of Multi-Layered TIPS Microspheres

The following method is used to create multi-layered microspheres consisting of an outer shell comprising 7.5% (w/v) poly(lactide-co-glycolide) (PLGA) in dimethyl carbonate and an inner core comprising 15% (w/v) PLGA in dimethyl carbonate (DMC).
 1. Solutions of PLGA (7.5 wt % or 15 wt % in DMC) were loaded into separate 10 ml syringes.
 2. The two syringes containing the polymer solutions were attached to a syringe pump and delivered via tubing at a rate of 3 ml/min to a Nisco Var D Classic open electromagnetically driven single nozzle encapsulator unit fitted with a stainless steel coaxial nozzle consisting of two subnozzles positioned coaxially (FIG. 14). The encapsulator unit was set to 1.80 kHz and 100% amplitude.
 3. The polymer droplets were collected in a liquid nitrogen quenching bath, transferred to a container and lyophilized for 24 hours until removal of the solvent was complete.
 4. The multi-layered microspheres were bisected and imaged using scanning electron microscopy (FIG. 15).

FIG. 16 illustrates further SEM images of microspheres produced using the method described above.

All cited references are herein incorporated in their entirety.

The invention claimed is:
1. A method for attaching a therapeutic agent to a hydrophobic microsphere structure produced by thermally induced phase separation comprising:
 i) at least partly submerging the hydrophobic microsphere structure in a culture medium;
 ii) subsequently contacting the hydrophobic microsphere structure with a wetting agent that wets the hydrophobic microsphere structure, wherein the wetting agent is ethanol which is added to the culture medium to a concentration of from 10% to 30%; and iii) attaching the therapeutic agent to the hydrophobic microsphere structure.

2. The method of claim 1 which results in the hydrophobic microsphere structure being fully submerged in the culture medium.

3. The method of claim 1 wherein the hydrophobic microsphere structure comprises poly(lactide-co-glycolide) (PLGA).

4. The method of claim 1 wherein the culture medium is Dulbecco's Modified Eagle's Medium (DMEM).

5. The method of claim 1 wherein the culture medium is tissue culture medium comprising serum.

6. The method of claim 1 wherein the hydrophobic microsphere structure is mixed with the culture medium before and after the contacting with the wetting agent.

7. The method of claim 1 further comprising incubating the hydrophobic microsphere structure at about 30° C. to about 40° C.

8. The method of claim 1 wherein the therapeutic agent is a cell.

9. The method of claim 1 wherein the therapeutic agent is an active pharmaceutical ingredient (API).

10. The method of claim 1 further comprising periods of static incubation interspersed with agitation.

11. The method of claim 10 comprising about 1 minute of agitation at about 300 rpm per hour of static incubation.

12. The method of claim 5 wherein the serum is fetal bovine serum (FBS) or fetal calf serum (FCS).

* * * * *